United States Patent
Zaiki

(10) Patent No.: US 9,895,118 B2
(45) Date of Patent: Feb. 20, 2018

(54) X-RAY DIAGNOSTIC APPARATUS

(71) Applicant: Toshiba Medical Systems Corporation, Otawara (JP)

(72) Inventor: Ryuji Zaiki, Utsunomiya (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 365 days.

(21) Appl. No.: 14/823,203

(22) Filed: Aug. 11, 2015

(65) Prior Publication Data

US 2015/0342546 A1  Dec. 3, 2015

Related U.S. Application Data

(63) Continuation of application No. PCT/JP2014/053530, filed on Feb. 14, 2014.

(30) Foreign Application Priority Data

Feb. 14, 2013 (JP) ................................. 2013-026638
Feb. 14, 2014 (JP) ................................. 2014-026492

(51) Int. Cl.
*A61B 1/00* (2006.01)
*A61B 6/00* (2006.01)
(Continued)

(52) U.S. Cl.
CPC ............ *A61B 6/4441* (2013.01); *A61B 6/022* (2013.01); *A61B 6/08* (2013.01); *A61B 6/4482* (2013.01);
(Continued)

(58) Field of Classification Search
None
See application file for complete search history.

(56) References Cited

U.S. PATENT DOCUMENTS

2013/0230136 A1* 9/2013 Sakaguchi ............. H04N 13/00
378/41
2014/0039303 A1* 2/2014 Kanzaki ................... A61B 6/12
600/424
(Continued)

FOREIGN PATENT DOCUMENTS

JP  2011-72655 A  4/2011
JP  2011-181991 A  9/2011
(Continued)

OTHER PUBLICATIONS

International Search Report issued May 13, 2014 for PCT/JP2014/053530 filed on Feb. 14, 2014 with English Translation.
(Continued)

*Primary Examiner* — Hoon Song
(74) *Attorney, Agent, or Firm* — Oblon, McClelland, Maier & Neustadt, L.L.P.

(57) ABSTRACT

An X-ray diagnostic apparatus according to one embodiment comprises: an X-ray tube, an X-ray detector, a supporting arm configured to support the X-ray tube and the X-ray detector in directions to face each other, a moving mechanism configured to move the supporting arm around a plurality of rotation axes and processing circuitry configured to set an imaging sequence concerning a plurality of left-eye imaging positions with respect to the object and a plurality of right-eye imaging positions respectively corresponding to the plurality of left-eye imaging positions and configured to control the moving mechanism to move the supporting arm in accordance with the set imaging sequence. The imaging sequence includes a sequence of continuously performing imaging at at least two of the plurality of left-eye imaging positions or a sequence of continuously performing imaging at at least two of the plurality of right-eye imaging positions.

10 Claims, 16 Drawing Sheets

(51) Int. Cl.
*A61B 6/02* (2006.01)
*A61B 6/08* (2006.01)

(52) U.S. Cl.
CPC .............. *A61B 6/463* (2013.01); *A61B 6/467* (2013.01); *A61B 6/469* (2013.01); *A61B 6/503* (2013.01); *A61B 6/504* (2013.01); *A61B 6/545* (2013.01)

(56) References Cited

U.S. PATENT DOCUMENTS

2015/0150527 A1* 6/2015 Ohishi .................... A61B 6/504
378/62
2015/0223769 A1* 8/2015 Imagawa ............... A61B 6/022
348/54

FOREIGN PATENT DOCUMENTS

| JP | 2011-259373 A | 12/2011 |
| JP | 2012-080294 A | 4/2012 |
| JP | 2012-170670 A | 9/2012 |
| JP | 2013-233318 A | 11/2013 |
| WO | WO 2013/168500 A1 | 11/2013 |

OTHER PUBLICATIONS

Written Opinion issued May 13, 2014 for PCT/JP2014/053530 filed on Feb. 14, 2014.

* cited by examiner

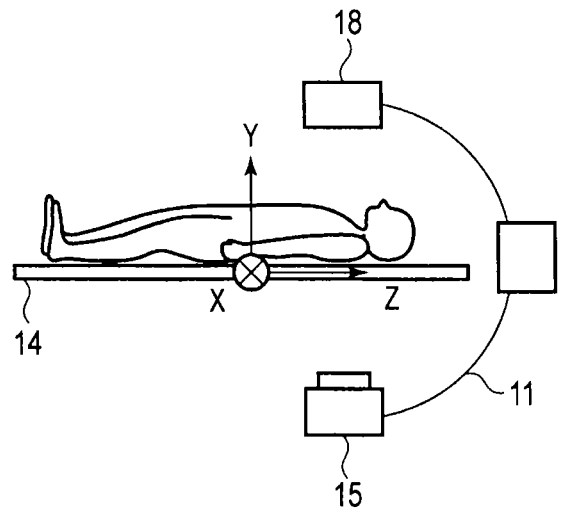
F I G. 3B
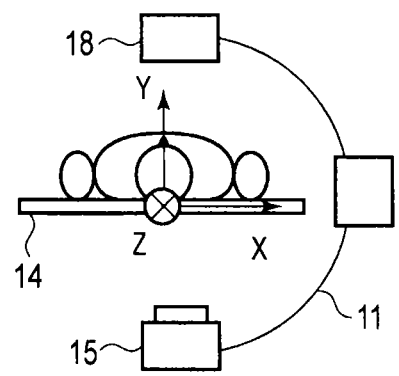
F I G. 3C

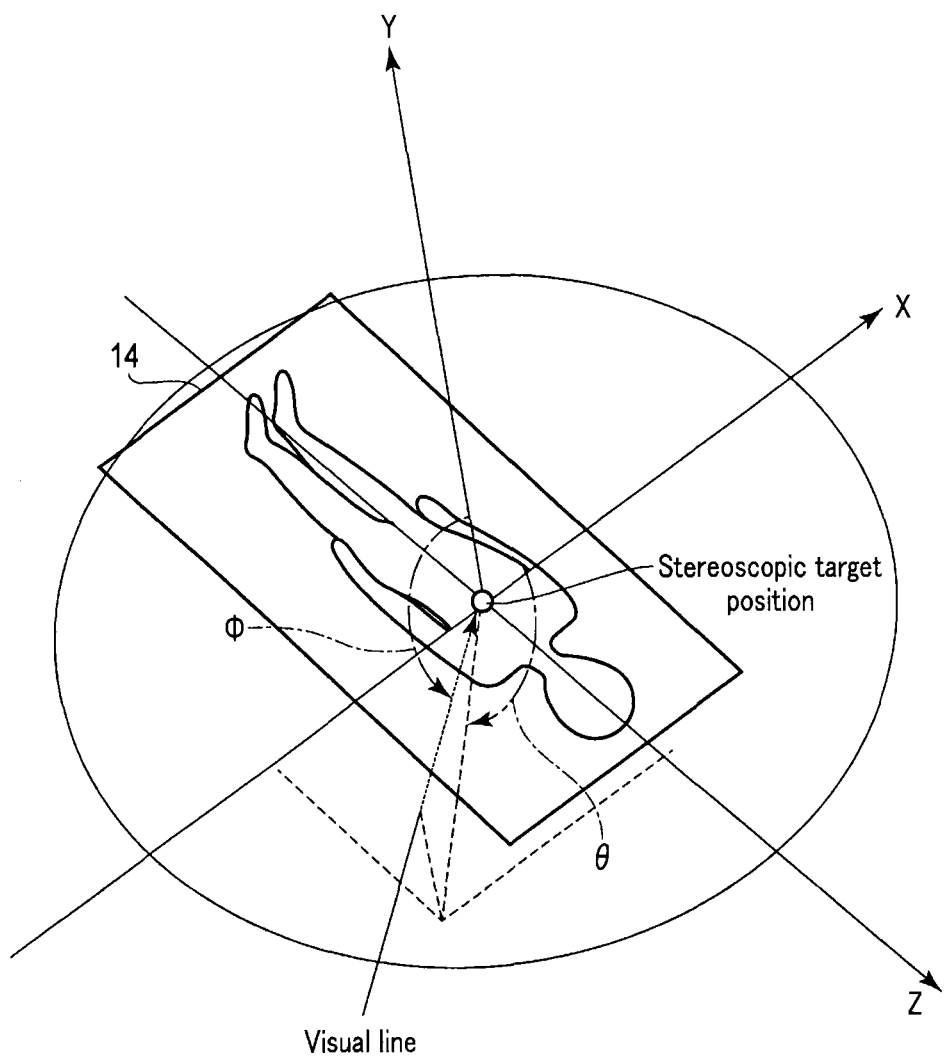
F I G. 4

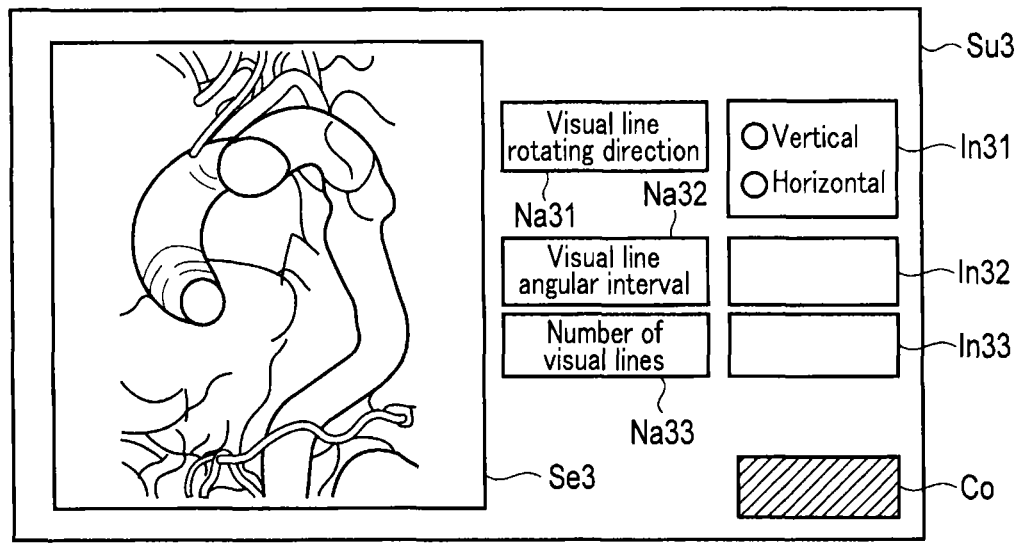
F I G. 7A
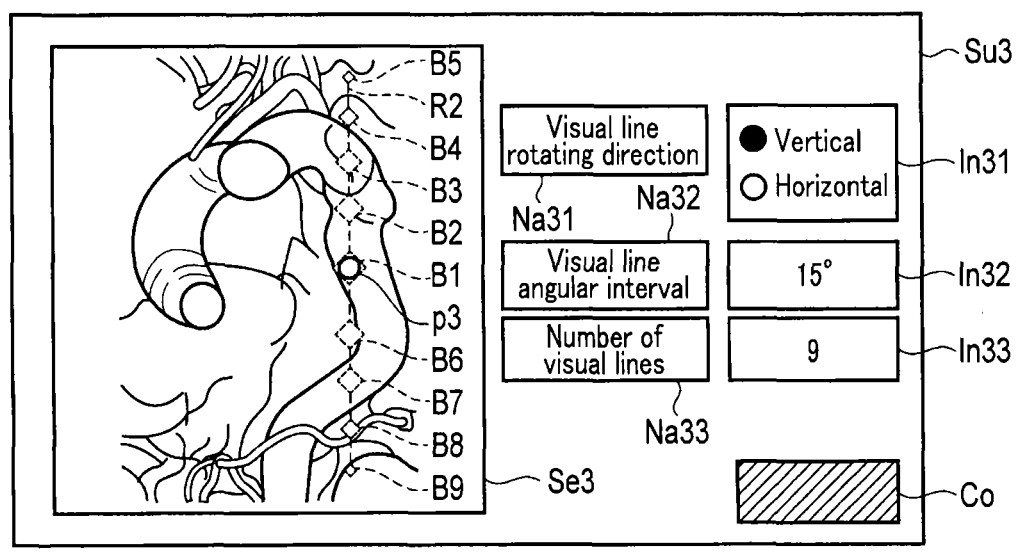
F I G. 7B

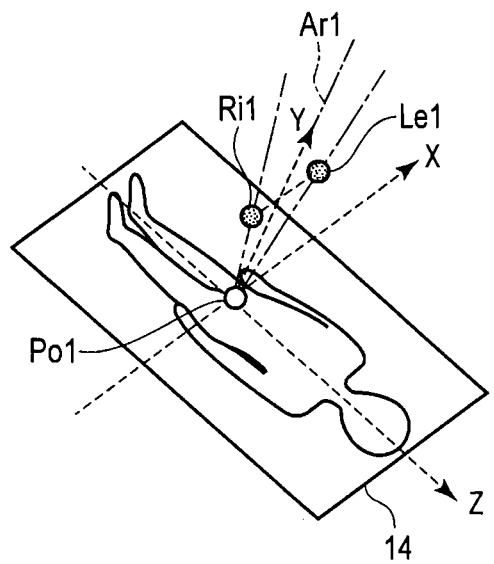
F I G. 8A
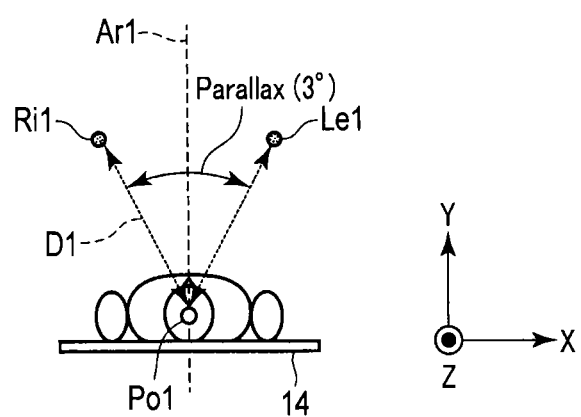
F I G. 8B

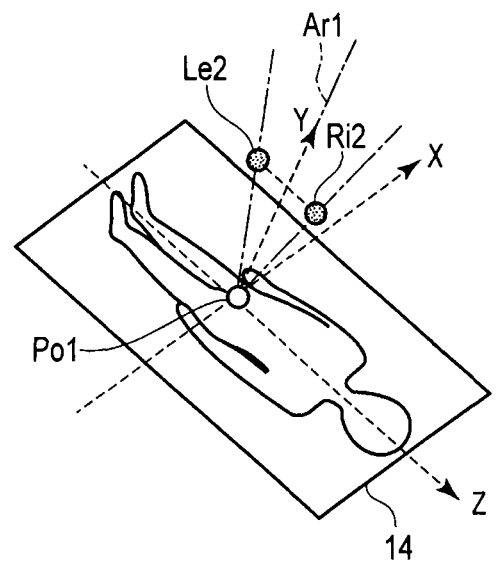
F I G. 9A
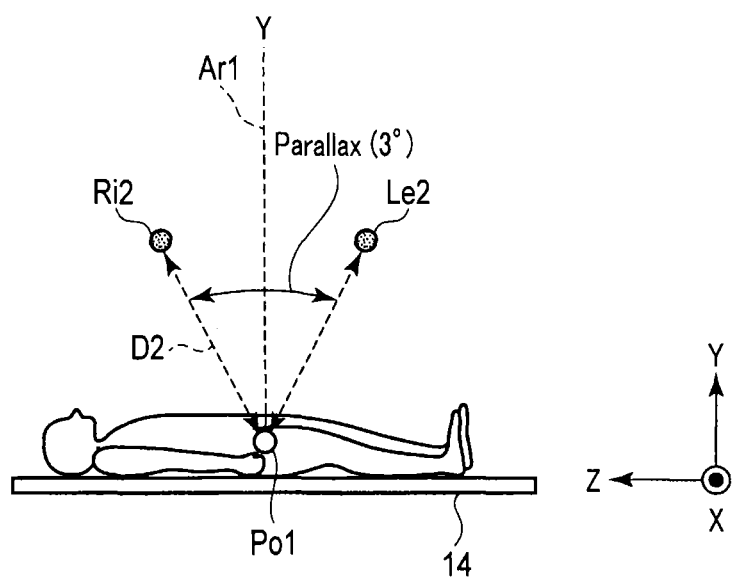
F I G. 9B

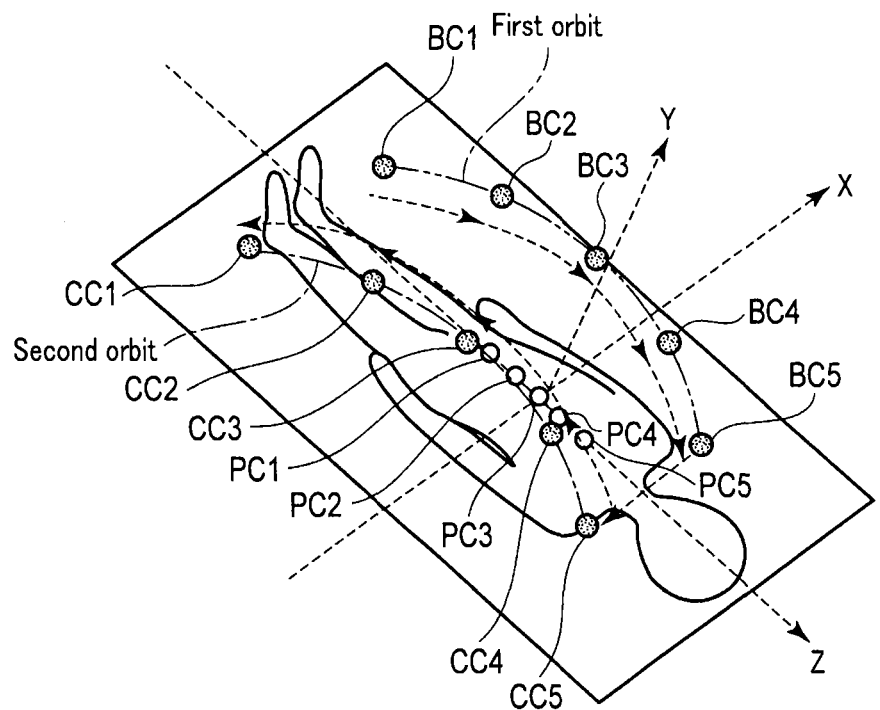
F I G. 12A
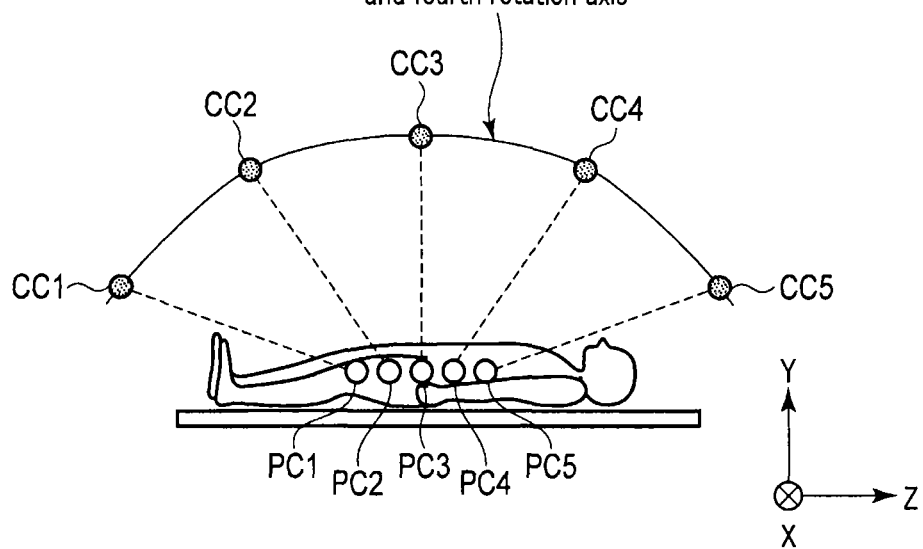
F I G. 12B

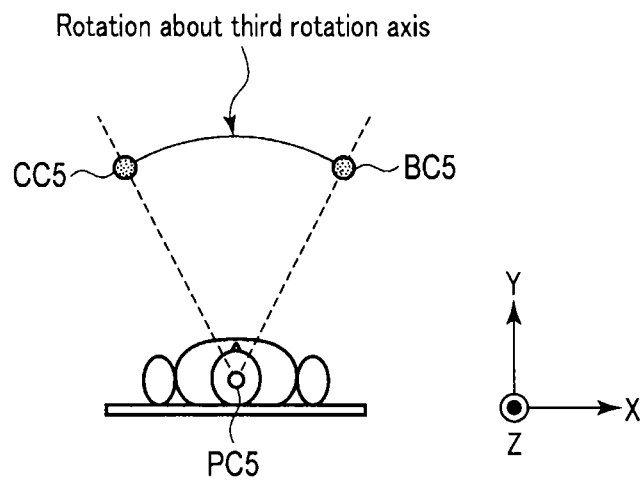
F I G. 12C
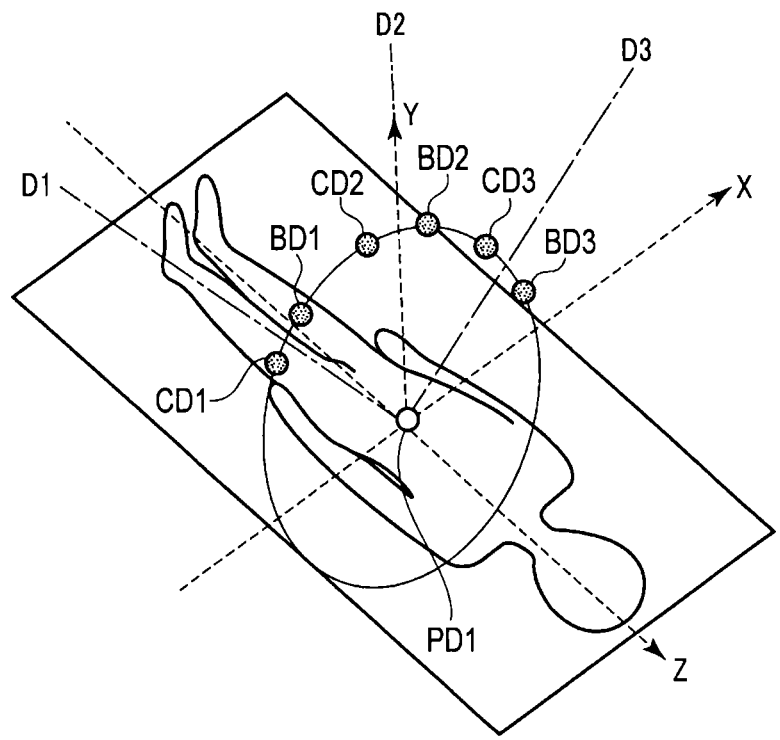
F I G. 13

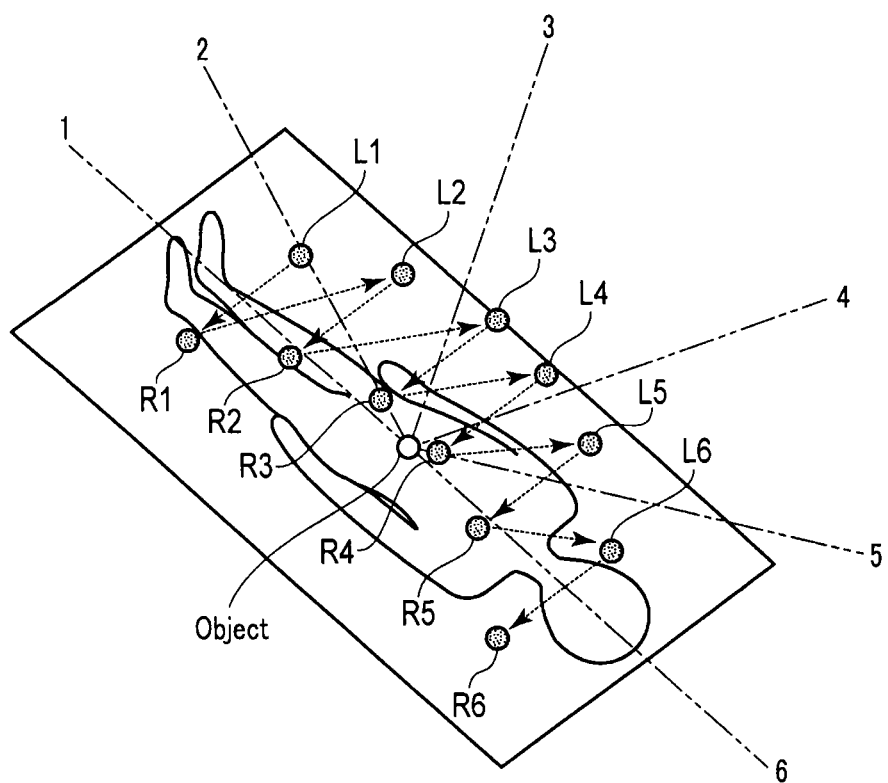
F I G. 15

X-RAY DIAGNOSTIC APPARATUS

CROSS-REFERENCE TO RELATED APPLICATIONS

This application is a Continuation Application of PCT Application No. PCT/JP2014/053530, filed Feb. 14, 2014 and based upon and claims the benefits of priority from the Japanese Patent Application No. 2013-026638, filed Feb. 14, 2013 and priority from the Japanese Patent Application No. 2014-026492, filed Feb. 14, 2014, the entire contents of all of which are incorporated herein by reference.

FIELD

Embodiments described herein relate generally to an X-ray diagnostic apparatus.

BACKGROUND

There is available a stereoscopic vision technique of allowing stereoscopic viewing of an image by displaying a left-eye image and a right-eye image having an angular difference on a monitor. Stereoscopic vision allows the user to easily grasp the forward/backward relationship between objects and the unevenness information of an object surface, which are difficult to know on a general two-dimensional display. When the stereoscopic vision technique is applied to the medical field, for example, an X-ray diagnostic apparatus including a C-arm acquires a left-eye image corresponding to a visual line direction at the preset stereoscopic target position of an object, and then acquires a right-eye image corresponding to the visual line direction at the stereoscopic target position of the object upon rotating the C-arm. The left- and right-eye images are then displayed to allow the user to stereoscopically view the stereoscopic target position of the object from the visual line direction. The user can stereoscopically recognize the stereoscopic target position of the object from the visual line direction by viewing the display unit at a specific position. In addition, acquiring images while rotating the C-arm in a lateral direction (around the body axis) allows the user to stereoscopically recognize the stereoscopic target position of the object from a plurality of directions laterally shifted from each other. In this manner, the user stereoscopically recognizes the stereoscopic target position of the object to precisely grasp, for example, the complex positional relationship between blood vessels. This makes it possible to perform safer and more accurate surgical operations and the like.

However, for example, the user sometimes wants to see a recognized stereoscopic vision video upon rotating it up, down, left, and right. Assume that the user wants to recognize a stereoscopic vision video concerning the stereoscopic target position of an object from six upper and lower directions. In this case, as shown in FIG. 15, six visual lines (visual lines 1 to 6 in FIG. 15) are set with respect to the stereoscopic target position of the object. A left-eye imaging position and a right-eye imaging position are set for one visual line. When performing imaging at these imaging positions, the apparatus acquires first a left-eye image corresponding to a direction 1 at an imaging position L1, and then acquires a right-eye image corresponding to the direction 1 at an imaging position R1 upon rotating the C-arm toward the imaging position R1. The apparatus then rotates the C-arm toward an imaging position L2 to acquire a left-eye image corresponding to a direction 2 at the imaging position L2, and acquires a right-eye image corresponding to the direction 2 at an imaging position R2 upon rotating the C-arm toward the imaging position R2. This reversing operation of the C-arm is repeatedly executed in accordance with the number of visual lines. The reversing operation of the C-arm imposes heavy load on the moving mechanism of the C-arm. For this reason, an increase in the number of times of the reversing operation of the C-arm may lead to a failure or the like in the C-arm. Stereoscopic vision has been described so far, but the same applies to a case in which an object is imaged continuously or intermittently from a plurality of directions. Setting an imaging sequence in disregard of the load will increase the number of times of starting the rotation of the C-arm, the number of times of stopping the rotation, a total rotational angle, and the number of times of switching a rotation axis. This may lead to a cause of a failure or the like in the C-arm.

It is an object to provide an X-ray diagnostic apparatus which suppresses a load on a mechanism associated with rotation when imaging an object continuously or intermittently from a plurality of directions.

Solution to Problem

BRIEF DESCRIPTION OF DRAWINGS

FIG. 3B is a view showing the positional relationship between a top and the C-arm when FIG. 3A is viewed from the —X-axis direction.

FIG. 3C is a view showing the positional relationship between the top and the C-arm when FIG. 3A is viewed from the +Z-axis direction.

FIG. 4 is a view for explaining a visual line angle.

FIG. 7A is a view showing the third example of the visual line setting support screen.

FIG. 7B is a view showing the third example of the visual line setting support screen after a plurality of visual lines are input.

FIG. 8A is a view showing the first example of the positional relationship between the stereoscopic target position of the patient placed on the top, a visual line direction, and a display direction.

FIG. 8B is a view when FIG. 8A is viewed from the +Z-axis direction.

FIG. 9A is a view showing the second example of the positional relationship between the stereoscopic target position of the patient placed on the top, a visual line direction, and a display direction.

FIG. 9B is a view when FIG. 9A is viewed from the +X-axis direction.

FIG. 10A is viewed from the −X-axis.

FIG. 10A is viewed from the +Z-axis.

FIG. 11A is viewed from the −X-axis.

FIG. 11A is viewed from the +Z-axis.

FIG. 12A is a perspective view showing the second example of a plurality of imaging positions.

FIG. 12B is a view when FIG. 12A is viewed from the −X-axis.

FIG. 12C is a view when FIG. 12A is viewed from the +Z-axis.

FIG. 13 is a view showing the fourth example of a plurality of imaging positions set by an imaging position setting unit.

FIG. 15 is a view showing the first example of the movement sequence of the C-arm of the X-ray diagnostic apparatus to a plurality of imaging positions according to a related art.

DETAILED DESCRIPTION

Figure 1:
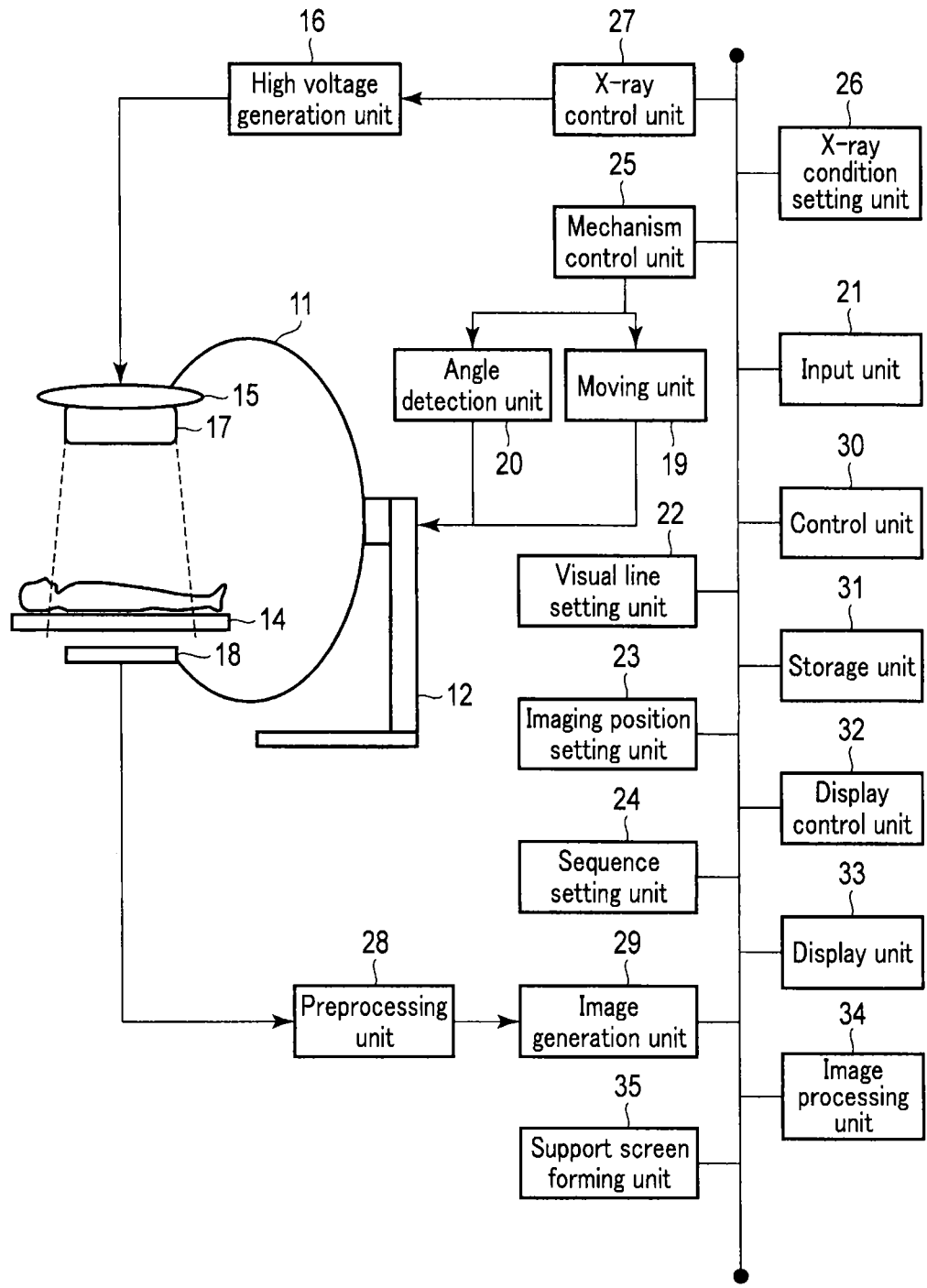
FIG. 1 is a block diagram showing an example of the arrangement of an X-ray diagnostic apparatus according to this embodiment.

According to one embodiment, there is provided that an X-ray diagnostic apparatus which comprises an X-ray tube configured to generate X-rays, an X-ray detector configured to detect X-rays generated from the X-ray tube and transmitted through an object, a supporting arm configured to support the X-ray tube and the X-ray detector in directions to face each other, a moving mechanism configured to move the supporting arm around a plurality of rotation axes and processing circuitry configured to set an imaging sequence concerning a plurality of left-eye imaging positions with respect to the object and a plurality of right-eye imaging positions respectively corresponding to the plurality of left-eye imaging positions and configured to control the moving mechanism to move the supporting arm in accordance with the set imaging sequence. The imaging sequence includes a sequence of continuously performing imaging at at least two of the plurality of left-eye imaging positions or a sequence of continuously performing imaging at at least two of the plurality of right-eye imaging positions.

An X-ray diagnostic apparatus according to this embodiment will be described below with reference to the accompanying drawings. Note that the X-ray diagnostic apparatus according to the embodiment aims at suppressing a load on a mechanism associated with the rotation of a holding unit (e.g., a C-arm) when imaging an object from a plurality of directions. It is especially effective in imaging with the purpose of implementing stereoscopic vision of an object from a plurality of directions or a plurality of positions. The embodiment will therefore exemplify an X-ray diagnostic apparatus configured to execute imaging with the purpose of implementing stereoscopic vision of an object from a plurality of directions or a plurality of positions. Note that the same reference numerals in the following description denote constituent elements having almost the same functions and arrangements, and a repetitive description will be made only when required.

FIG. 1 is a block diagram showing an example of the arrangement of the X-ray diagnostic apparatus according to this embodiment. As shown in FIG. 1, the X-ray diagnostic apparatus includes a C-arm 11, a C-arm holding mechanism 12 (C-arm holding mechanism), a bed 13, a top 14, an X-ray generation unit 15, a high voltage generation unit 16, an X-ray stop 17, an X-ray detection unit 18, a moving unit 19, an angle detection unit 20, an input unit 21, a visual line setting unit 22, an imaging position setting unit 23, a sequence setting unit 24, a mechanism control unit 25, an X-ray condition setting unit 26, an X-ray control unit 27, a preprocessing unit 28, an image generation unit 29, a control unit 30, a storage unit 31 such as a memory, a display control unit 32, a display unit 33, an image processing unit 34, and a support screen forming unit 35.

The gantry unit of the X-ray diagnostic apparatus includes the C-arm 11, the C-arm holding mechanism 12, the bed 13, and the top 14. The C-arm holding mechanism 12 rotatably holds the C-arm 11. The C-arm 11 holds the X-ray generation unit 15 on its one end. The X-ray generation unit 15 is a vacuum tube which generates X-rays. The X-ray generation unit 15 generates X-rays upon reception of a high voltage (tube voltage) from the high voltage generation unit 16. The X-ray generation unit 15 has a radiation window for radiating generated X-rays. The X-ray stop 17 is attached to the radiation window of the X-ray generation unit 15. The X-ray stop 17 is a beam cone limiter which can adjust an X-ray irradiation field on the detection surface of the X-ray detection unit 18. Adjusting an X-ray irradiation field by using the X-ray stop 17 can reduce unnecessary radiation exposure on an object. The C-arm 11 holds the X-ray detection unit 18 on the other end so as to make it face the X-ray generation unit 15. The X-ray detection unit 18 includes a plurality of X-ray detection elements. The plurality of X-ray detection elements are arranged in a two-dimensional array. A detector in a two-dimensional array is called an FPD (Flat Panel Detector). Each element of the FPD detects the X-rays emitted from the X-ray generation unit 15 and transmitted through the object. Each element of the FPD outputs an electrical signal corresponding to a detected X-ray intensity. A line connecting the focus of the X-ray generation unit 15 and the central position of the X-ray detection surface of the X-ray detection unit 18 is called an imaging axis (the fifth rotation axis). The rotation of the X-ray detection unit 18 about the fifth rotation axis determines the top and bottom of an obtained image.

Note that in this embodiment, it is described that the C-arm 11 supports the X-ray generation unit 15 and the X-ray detection unit 18, and the C-arm holding mechanism 12 moves the C-arm 11 by a motor and rotatably holds the C-arm 11. However, other support mechanisms may be used as long as they can hold the X-ray generation unit 15 and the X-ray detection unit 18 so as to make them face each other. For example, the C-arm 11 and the C-arm holding mechanism 12 can be replaced with a first holding unit which rotatably holds the X-ray generation unit 15 and a second holding unit which rotatably holds the X-ray detection unit 18. In this case, for example, the first holding unit has a mechanism mounted on the floor. The second holding unit has a mechanism suspended from the ceiling. The first and second holding units hold the X-ray generation unit 15 and the X-ray detection unit 18 in directions in which they face each other. It is possible to perform continuous X-ray imaging by, for example, controlling the first and second holding units so as to synchronize their rotating operations.

Figure 2:
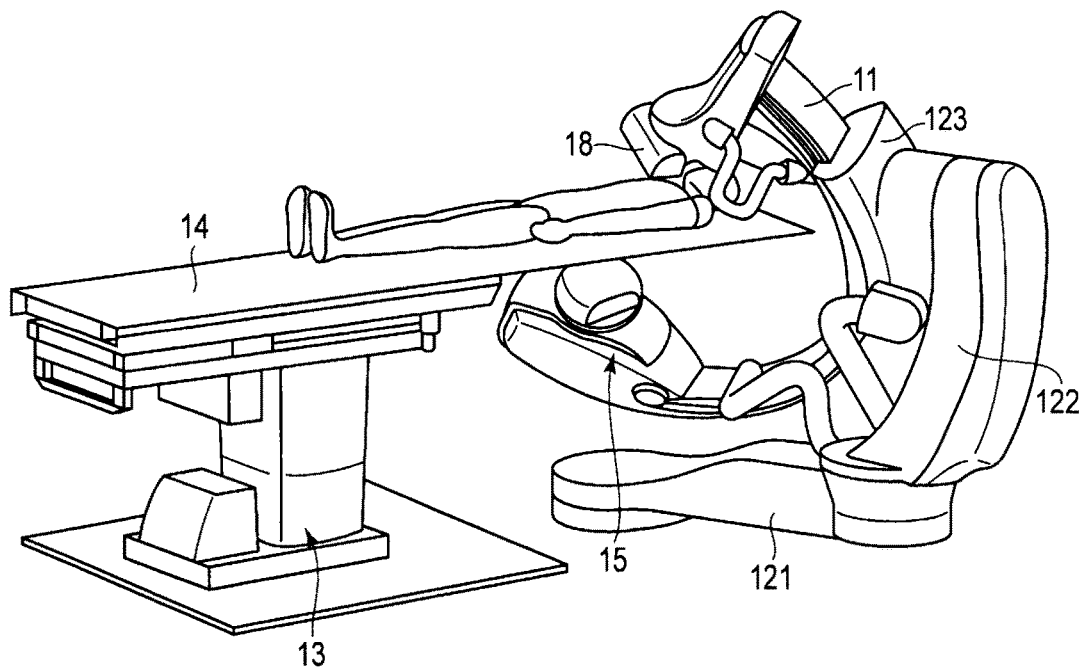
FIG. 2 is a perspective view showing an outer appearance of the gantry unit of the X-ray diagnostic apparatus according to this embodiment.

FIG. 2 is a perspective view showing an outer appearance of the gantry unit of the X-ray diagnostic apparatus according to this embodiment. Note that the C-arm holding mechanism 12 may be of either a ceiling suspension type that holds the C-arm 11 while suspending it from the ceiling or a floor mount type that holds the C-arm 11 mounted on the floor or may be a biplane mechanism capable of imaging an object simultaneously from two directions by combining the ceiling suspension type and the floor mount type. This embodiment will exemplify the floor mount type. The C-arm holding mechanism 12 includes a floor swivel arm 121, a stand 122, and an arm holder 123. The floor swivel arm 121 is provided, at its one end, on the floor surface so as to freely swivel about the first rotation axis. The stand 122 is held on the other end of the floor swivel arm 121 so as to be rotatable about the second rotation axis. The first and second rotation axes are almost parallel to the orthogonal axis. The arm holder 123 is held on the stand 122 so as to be rotatable about the third rotation axis. The third rotation axis is an axis almost orthogonal to the orthogonal axis. The C-arm 11 is held on the arm holder 123 so as to freely rotate (slide/rotate) in an arc along the shape of the C-arm 11. The rotation axis of this sliding rotation is called the fourth rotation axis. While there is no rotation about the second rotation axis, the first axis, the third axis, the fourth axis, and the fifth axis intersect at one point called an isocenter. At the time of X-ray imaging, the user moves the C-arm 11 so as to match the isocenter with a stereoscopic target position.

The bed 13 and the top 14 are arranged between the X-ray generation unit 15 and the X-ray detection unit. The bed 13 holds the top 14, on which an object is placed, so as to make the top 14 movable with respect to three orthogonal axes. Assume that the three orthogonal axes are defined by, for example, the short axis of the top 14, the long axis of the top 14, and an orthogonal axis orthogonal to the short- and long-axes. A direction along the long axis of the top 14 will be referred to as a long-axis direction. In addition, a direction along the short axis of the top 14 will be referred to as a short-axis direction. In addition, a direction along the orthogonal axis will be referred to as an orthogonal-axis direction.

The moving unit 19 rotates the C-arm 11 about the first to fifth rotation axes under the control of the mechanism control unit 25 by a motor. In addition, the moving unit 19 makes the top 14 slide in the long-axis direction or the short-axis direction and makes it move up and down in the orthogonal-axis direction under the control of the mechanism control unit 25. In addition, the moving unit 19 rotates and moves the top 14 so as to tilt it with respect to the mounting surface of the bed 13 by using, as a rotation axis, an axis parallel to at least one of the long-axis direction and the short-axis direction. In the following description, sliding movement, up/down movement, and rotation/movement concerning the movement of the C-arm 11 will be collectively referred to as movement.

Figure 3A:
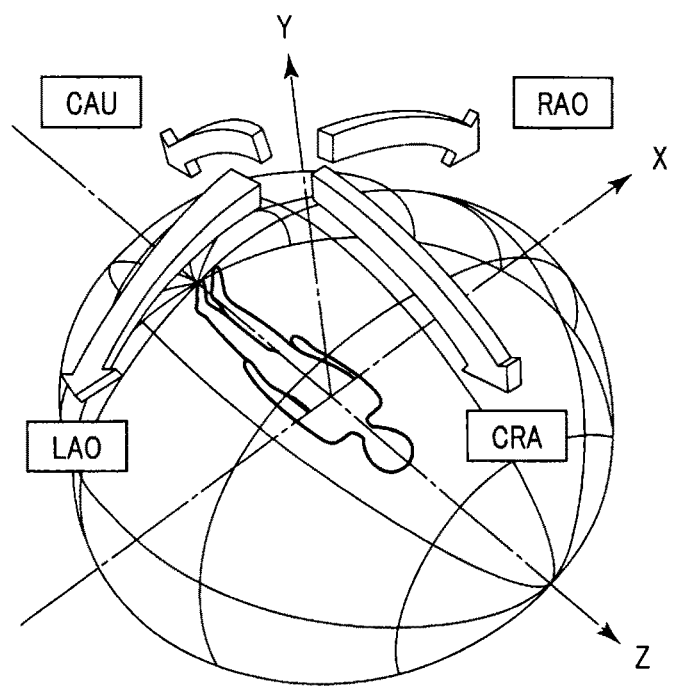
FIG. 3A is a view for explaining a schematic example of the moving direction of the C-arm of the X-ray diagnostic apparatus according to this embodiment.

FIG. 3A is a view for explaining a schematic example of the moving direction of the C-arm 11 of the X-ray diagnostic apparatus according to this embodiment. The coordinate system is a three-dimensional spatial coordinate system (to be referred to as a top coordinate system hereinafter), with the central position of the top 14 surface being an origin, the short-axis direction being the X-axis, the orthogonal-axis direction being the Y-axis, and the long-axis direction being the Z-axis when the top 14 is placed at a predetermined position. As shown in FIG. 3A, the first direction is defined by the first oblique position (Right Anterior Oblique view: to be referred to as RAO hereinafter) and the second oblique position (Left Anterior Oblique view: to be referred to as LAO hereinafter). The second direction is defined by the cranial direction (CRAnial: to be referred to as CRA hereinafter) and the caudal direction (CAUdal: to be referred to as CAU hereinafter).

FIG. 3B is a view showing the positional relationship between the top 14 and the C-arm 11 when FIG. 3A is viewed from the −X-axis direction. As shown in FIG. 3B, when the C-arm 11 is arranged on the patient head side, the moving unit 19 rotates the C-arm 11 in the first direction by rotating the arm holder 123 about the third rotation axis under the control of the mechanism control unit 25. In addition, the moving unit 19 rotates the C-arm 11 in the second direction by sliding/rotating the C-arm 11 about the fourth rotation axis under the control of the mechanism control unit 25.

FIG. 3C is a view showing the positional relationship between the top 14 and the C-arm 11 when FIG. 3A is viewed from the +Z-axis direction. As shown in FIG. 3C, when the C-arm 11 is arranged on the patient's left side, the moving unit 19 rotates the C-arm 11 in the first direction by sliding/rotating the C-arm 11 about the fourth rotation axis under the control of the mechanism control unit 25. In addition, the moving unit 19 rotates the C-arm 11 in the second direction by rotating the arm holder 123 about the third rotation axis under the control of the mechanism control unit 25. The moving unit 19 moves the C-arm 11 arranged on the patient head side as shown in FIG. 3B to the patient's left side as shown in FIG. 3C while maintaining the position of the isocenter by rotating the floor swivel arm 121 about the first rotation axis under the control of the mechanism control unit 25. It is therefore possible to change an imaging angle with respect to the object moved to the isocenter by rotating the floor swivel arm 121 about the first rotation axis, rotating the arm holder 123 about the third rotation axis, and sliding/rotating the C-arm 11 about the fourth rotation axis.

In addition, the moving unit 19 moves the C-arm 11 in the long-axis direction and the short-axis direction by rotating the floor swivel arm 121 about the first rotation axis and rotating the stand 122 about the second rotation axis under the control of the mechanism control unit 25. This makes it possible to change the imaging position without moving the patient. Note that the imaging position may be changed by moving the patient without moving the C-arm 11. At this time, the moving unit 19 moves the top 14 in the long-axis direction and the short-axis direction under the control of the mechanism control unit 25.

The angle detection unit 20 detects five rotational angles respectively corresponding to the first to fifth rotation axes.

The input unit 21 functions as an interface for accepting instruction information issued by the user with respect to the X-ray diagnostic apparatus. As the input unit 21, an input device such as a mouse, keyboard, trackball, touch panel, or buttons can be used as needed. More specifically, the input unit 21 includes an operation console for moving the C-arm 11 in accordance with a user instruction. The operation console includes, for example, buttons, a handle, and a trackball which are used to rotate the C-arm 11 about the above rotation axes independently. Instruction information includes, for example, an X-ray condition setting instruction, a parallax condition setting instruction, and a visual line setting instruction.

X-ray conditions include, for example, a tube current, a tube voltage, and an imaging time. The user inputs these parameters by operations on the X-ray condition setting screen displayed on the display unit 33.

Parallax conditions are conditions for determining a parallax. Parallax conditions include parameters such as an inter-pupil distance and a reference user distance. The user distance is the distance from the display central position of the display unit 33 to the user. The reference user distance is the distance from the position at which the user mainly visually recognizes the display unit 33 to the display unit 33 (to be referred to as the reference position hereafter). The inter-pupil distance is the distance between the pupil central position of the right eye and the pupil central position of the left eye of the user. The control unit 30 stores data concerning the inter-pupil distance and the reference user distance input by the user in the storage unit 31 (to be described later), together with user information. Note that an inter-pupil distance and a reference user distance may be input by another method. For example, an inter-pupil distance and a reference user distance may be specified by a detection device such as a camera which can detect the face of a user. This makes it possible to automatically change the reference user distance even when the user has moved with respect to the display central position of the display unit 33. The user can therefore see a stereoscopic vision video even at the position of a destination. In addition, the data of an inter-pupil distance and a reference user distance may be selected as needed from the user information database stored in the storage unit 31 (to be described later) in accordance with a user instruction. In addition, the inter-pupil distance and the reference user distance are parameters which are used by the imaging position setting unit 23 (to be described later) when calculating a parallax. For this reason, it is possible to input a parallax as a parallax condition instead of inputting an inter-pupil distance and a reference user distance by the user.

A visual line is defined by a stereoscopic target position, a visual line direction, and a display direction. A stereoscopic target position is information for determining the central position of an object which the user wants to stereoscopically see. When implementing stereoscopic vision by the intersection technique, a stereoscopic target position overlaps the position of a convergence point at which the right- and left-eye visual lines intersect with each other. A visual line direction is information for determining a direction in which a stereoscopic target position is stereoscopically seen. A display direction is information for determining the top, bottom, left, and right of an object when a stereoscopic target position is seen from a visual line direction. Therefore, when a stereoscopic vision video corresponding to the visual line set by the user is recognized, the video is a stereoscopic vision video when the stereoscopic target position is seen from the visual line direction. The central position of the stereoscopic vision video corresponds to the stereoscopic target position. The top, bottom, left, and right of the stereoscopic vision video respectively correspond to the top, bottom, left, and right defined by the display direction. A visual line is formed by the support screen forming unit 35 (to be described later), and is input in accordance with a user operation on the visual line setting support screen displayed on the display unit 33 (to be described later).

The visual line setting unit 22 sets the visual line input by the user via the input unit 21. The visual line direction included in the visual line is represented by an angle (to be referred to as a visual line angle hereinafter) in the top coordinate system.

FIG. 4 is a view for explaining a visual line angle. FIG. 4 shows a state in which a patient is placed on his/her back on the top 14. For the sake of simplicity, assume that a stereoscopic target position is set at the origin of the top coordinate system. In addition, assume that an axis parallel to the long axis of the top 14 is the Z-axis, an axis parallel to the short axis of the top 14 is the X-axis, and an axis perpendicular to the top 14 surface is the Y-axis. As shown in FIG. 4, a visual line angle is represented by a first angle $\theta$ and a second angle $\varphi$. The first angle $\theta$ is the angle defined by a line indicating the visual line direction and the X-axis. The second angle $\varphi$ is the angle defined by a line indicating the visual line direction and the Y-axis.

The support screen forming unit 35 forms a visual line setting support screen displayed on the display unit 33 (to be described later). The visual line setting support screen is a screen for supporting the input of a visual line by the user. The support screen forming unit 35 arranges a plurality of components necessary for the user to set a visual line on a visual line setting support screen according to a predetermined arrangement method. A plurality of components include, for example, a visual line input image, a visual line confirmation image, an input button, a completion button, a name box, an input box, and a selection box. Of the plurality of components, components associated with images are generated by the image processing unit 34 (to be described later). The components such as the input button, the input box, and the name box are stored in the storage unit 31, together with information indicating each function. An example of a visual line setting support screen will be described below. A method of inputting a visual line will also be described with reference to FIGS. 5, 6A, 6B, 7A, and 7B.

Figure 5:
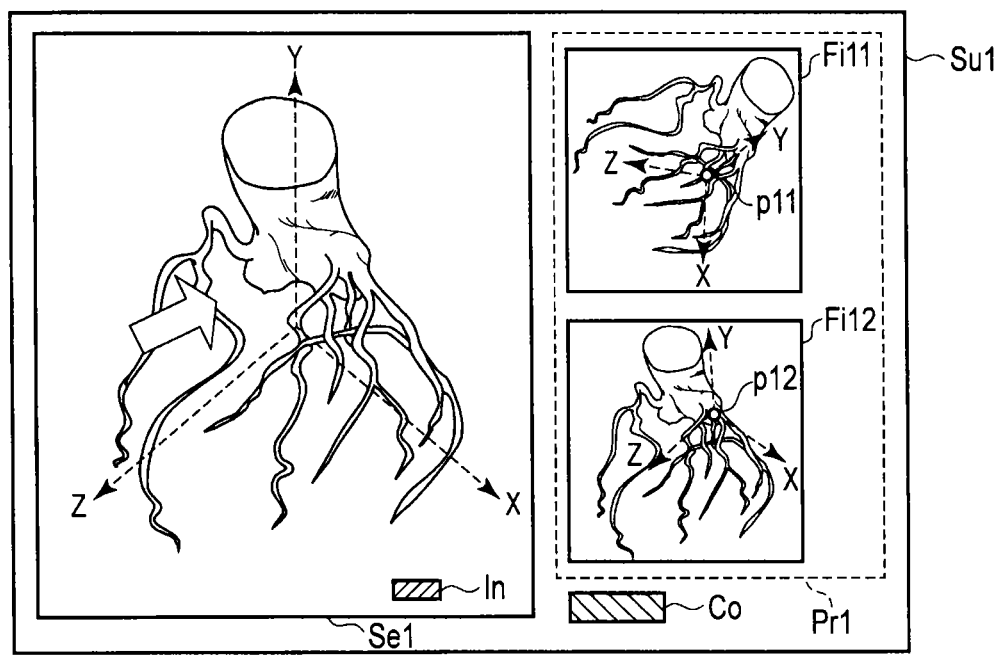
FIG. 5 is a view showing the first example of a visual line setting support screen.

FIG. 5 is a view showing the first example of a visual line setting support screen.

Referring to FIG. 5, reference symbol Su1 denotes a visual line setting support screen. The support screen forming unit 35 arranges a visual line input image Se1, an input confirmation area Pr1, an input button 1*n*, and a completion button Co on the visual line setting support screen Su1 in accordance with a predetermined arrangement method.

The visual line input image Se1 is a support image for allowing the user to input a visual line. The image processing unit 34 reconstructs the visual line input image Se1 based on the data of a plurality of X-ray images concerning an object. Referring to FIG. 5, the visual line input image Se1 is an image concerning a predetermined slice of a 3D image representing the blood vessel structure of the object. The user can input a stereoscopic target position, a visual line direction, and a display direction by operating the visual line input image Se1 with the mouse or the like.

For example, the user moves the cursor to a position corresponding to a stereoscopic target position by operating the mouse. The user then can input, as a stereoscopic target position, the position clicked with the mouse. The support screen forming unit 35 arranges a mark indicating the stereoscopic target position on the visual line input image Se1.

In addition, the user can switch to another slice of the 3D image representing the blood vessel structure of the object by rotating and moving the visual line input image Se1 with the mouse. At this time, the image processing unit 34 specifies a slice to be displayed in accordance with a mouse operation, and reconstructs the specified slice based on the data of a plurality of X-ray images concerning the object. The user then confirms a visual line direction and a display direction by pressing the input button 1*n*. With the above processing, the user can complete the input of one visual line. Note that the visual line direction corresponds to a direction (a direction perpendicular to a currently displayed slice) in which the user sees the visual line input image Se1 when he/she presses the input button 1*n*. In addition, a display direction (the top, bottom, left, and right of a video recognized as a stereoscopic vision video) corresponds to the top, bottom, left, and right of the image of the visual line input image Se1 when the input button ln is pressed. The user can input a plurality of visual lines by repeatedly performing the above visual line input operation. Note that the visual line input image Se1 displayed when the input button 1n is pressed is temporarily stored in the storage unit 31 as a visual line confirmation image. The support screen forming unit 35 then reads out the visual line confirmation image from the storage unit 31 and arranges it in the input confirmation area Pr1. Referring to FIG. 5, a visual line confirmation image Fi11 corresponding to a visual line 1 and a visual line confirmation image Fi11 corresponding to a visual line 2, which have already been input by the user, are displayed. The user checks the visual line confirmation image displayed in the input confirmation area Pr1, and can perform correction, deletion, or the like, as needed. When, for example, the user double-clicks on the visual line confirmation image Fi12, the support screen forming unit 35 rearranges the visual line confirmation image Fi12 as the visual line input image Se1. The user then corrects the visual line by performing the above operation using the mouse. Note that when the user sees a stereoscopic vision video corresponding to the visual line 1 (the visual line confirmation image Fi11) shown in FIG. 5, the video is a stereoscopic video of the visual line confirmation image Fi11. The central position of this video is a stereoscopic target position p11, and the top, bottom, left, and right of the video correspond to those of the visual line confirmation image Fi11.

The completion button Co is a button for notifying the visual line setting unit 22 of the completion of the input of a plurality of visual lines. The visual line setting unit 22 sets a plurality of visual lines in response to the pressing of the completion button Co. The imaging position setting unit 23 (to be described later) executes imaging position setting processing based on the visual lines set by the visual line setting unit 22.

The visual line input image Se1 is, for example, a 3D image concerning the object which is acquired in advance by this X-ray diagnostic apparatus. For this reason, the coordinate system of the visual line input image Se1 corresponds to the top coordinate system having a predetermined position on the top 14 as an origin. Therefore, this X-ray diagnostic apparatus can image the position of a patient corresponding to the position designated on the visual line input image Se1. Note that the coordinate system of the visual line input image Se1 corresponds to another coordinate system, for example, a patient coordinate system having a predetermined position on the patient as an origin or an arm coordinate system having a predetermined position on the C-arm 11 as an origin.

Note that the data of a plurality of X-ray images concerning the object is stored in the storage unit 31. Note that the data of a plurality of X-ray images concerning the object may be input from an external apparatus to this X-ray diagnostic apparatus. The external apparatus is, for example, an X-ray CT apparatus or PACS (Picture Archiving and Communication System). In this case, this X-ray diagnostic apparatus includes a communication interface unit for performing data communication with the external apparatus. The communication interface unit transmits an image acquisition request to the external apparatus under the control of the control unit 30. Image data corresponding to the acquisition request is received from the external apparatus. The received data is temporarily stored in the storage unit 31.

Referring to FIG. 5, the user inputs visual lines one by one by operating the mouse or the like on the visual line input image Se1. However, a plurality of visual lines may be input by another method.

A method different from the method of inputting a plurality of visual lines described with reference to FIG. 5 will be described with reference to FIGS. 6A and 6B.

Figure 6A:
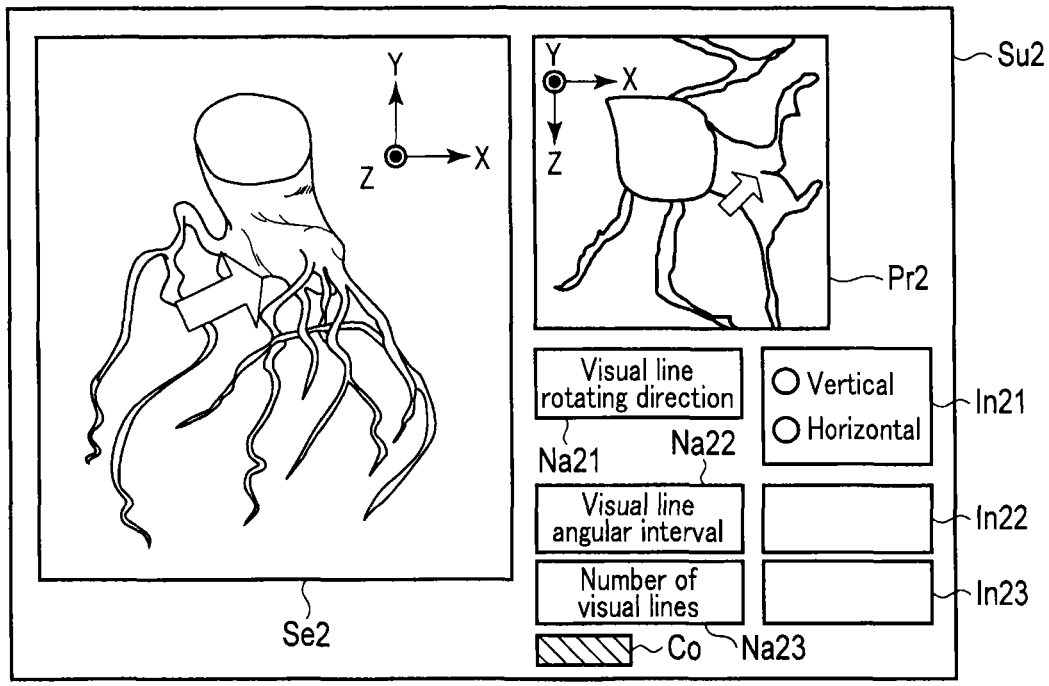
FIG. 6A is a view showing the second example of the visual line setting support screen.

FIG. 6A is a view showing the second example of a visual line setting support screen.

As shown in FIG. 6A, the support screen forming unit 35 arranges, on a visual line setting support screen Su2, a visual line input image Se2, an auxiliary image Pr2, a name box Na21 associated with a visual line rotating direction, a selection box ln21 for a visual line rotating direction, a name box Na22 associated with a visual line angular interval, an input box ln22 for a visual line angular interval, a name box Na23 associated with the number of visual lines, an input box ln23 for the number of visual lines, and the completion button Co in accordance with a predetermined arrangement method.

The visual line input image Se2 is identical to the visual line input image Se1. The auxiliary image Pr2 is an image concerning a slice of the 3D image representing the blood vessel structure of an object which is different from the visual line input image Se2. A slice of the visual line input image Se2 is preferably perpendicular to a slice of the auxiliary image Pr2. Referring to FIGS. 6A and 6B, the visual line input image Se2 is an image when the 3D image is seen from the Z direction, and the auxiliary image Pr2 is an image when the 3D image is seen from the Y direction. The auxiliary image Pr2 allows the user to easily recognize a depth direction on the visual line input image Se2. The selection box ln21 for a visual line rotating direction includes "horizontal" and "vertical" as selection items. The user can input a visual line rotating direction by selecting one of the selection items. A visual line rotating direction is a direction representing which direction the user wants to continuously see a stereoscopic vision video corresponding to a reference visual line. When the user selects "horizontal" as a visual line rotating direction, other visual lines are input to allow the user to continuously recognize a stereoscopic vision video corresponding to the reference visual line and identical stereoscopic vision videos in the horizontal direction. A visual line angular interval indicates an angle through which the stereoscopic vision video corresponding to the reference visual line is rotated. A reference visual line represents a reference for visual lines. A reference for visual lines is, for example, a visual line set first by the user in a series of medical treatments or the like concerning an object. A reference visual line is preferably set to a position, direction, and display direction in which the user should see an object most in a series of medical treatments or the like. The number of visual lines represents the number of visual lines to be set. The completion button Co is a button for notifying the visual line setting unit 22 of the completion of the input of visual lines.

Figure 6B:
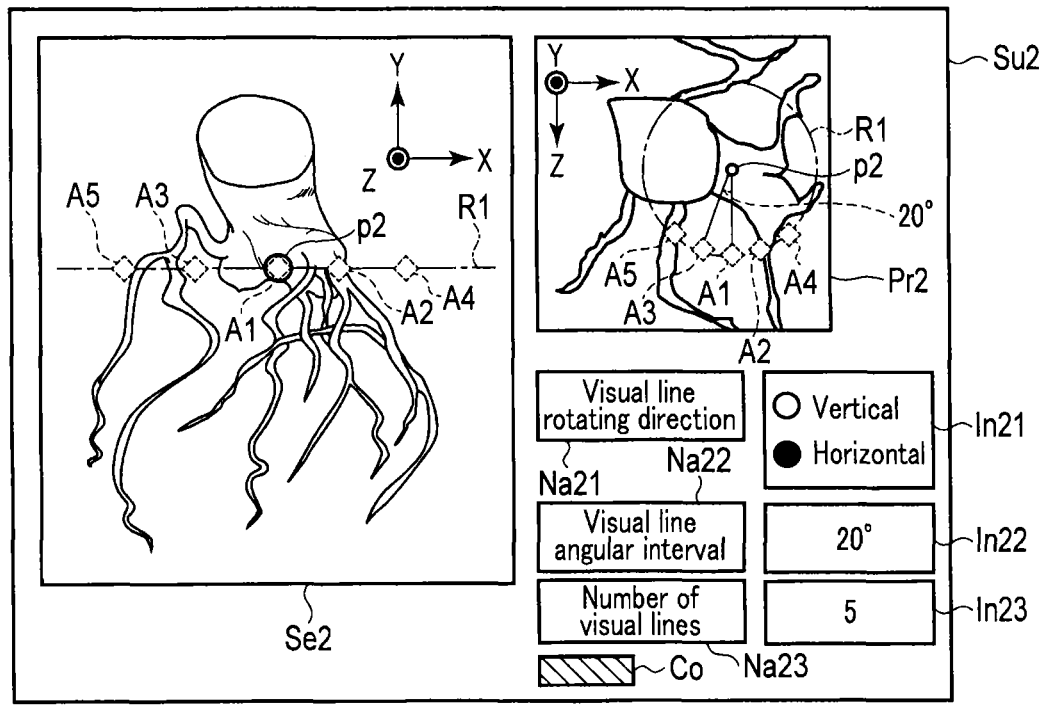
FIG. 6B is a view showing the second example of the visual line setting support screen after a plurality of visual lines are input.

FIG. 6B is a view showing the second example of the visual line setting support screen after a plurality of visual lines are input.

Referring to FIG. 6B, "horizontal", "20°", and "5" have been respectively input as a visual line rotating direction, a visual line angular interval, and the number of visual lines. In addition, a reference visual line A1 has been input by the user. The reference visual line A1 is represented by a reference stereoscopic target position p2, a reference visual line direction, and a reference display direction. A method of inputting the reference visual line A1 is the same as that described with reference to FIG. 5. That is, the user inputs the visual line input image Se2 by operating the mouse or the like. When a reference visual line is input on the visual line input image Se2, the support screen forming unit 35 arranges marks indicating the reference visual lines A1 on the visual line input image Se2 and the auxiliary image Pr2.

When "horizontal" is input as a visual line rotating direction, the support screen forming unit 35 arranges a line indicating a visual line rotating direction R1 in the horizontal direction, which passes through the mark indicating the reference visual line A1, on the visual line input image Se2. In addition, the line indicating the visual line rotating direction R1 passes through the mark indicating the reference visual line A1 and is arranged in the shape of a circle centered on the stereoscopic target position p2 on the auxiliary image Pr2 concerning a slice perpendicular to the visual line input image Se2.

The support screen forming unit 35 arranges a plurality of marks respectively corresponding to a plurality of visual lines on the line indicating the visual line rotating direction R1 according to the number of visual lines and the visual line angular interval which are input by the user. Referring to FIG. 6B, since the number of visual lines is "5" and the visual line angular interval is "20°", the support screen forming unit 35 arranges five marks corresponding to five visual lines (A1 to A5 in FIG. 6B) including the reference visual line A1. The five marks are arranged at angular intervals of 20°. As shown in FIG. 6B, the mark indicating the reference visual line A1 and the mark indicating the visual line A3 are arranged to form an angle of 20°. At this time, the vertex of the angle corresponds to the stereoscopic target position p2.

The user can correct an input visual line by a mouse operation on the visual line input image Se2 or the auxiliary image Pr2. For example, the user can correct the visual line A5 by moving the mark indicating the visual line A5 with the mouse. The visual line setting unit 22 sets a plurality of visual lines in response to pressing of the completion button Co.

Note that referring to FIGS. 5 and 6, a 3D image concerning an object is used as a visual line input image. However, a visual line input image may be a 2D image concerning an object. A method of inputting a plurality of visual lines by using a 2D image concerning an object will be described with reference to FIGS. 7A and 7B.

FIG. 7A is a view showing the third example of a visual line setting support screen.

As shown in FIG. 7A, the support screen forming unit 35 arranges, on a visual line setting support screen Su3, a visual line input image Se3, a name box Na31 associated with a visual line rotating direction, a selection box ln31 for a visual line rotating direction, a name box Na32 associated with a visual line angular interval, an input box ln32 for a visual line angular interval, a name box Na33 associated with the number of visual lines, an input box ln33 for the number of visual lines, and the completion button Co in accordance with a predetermined arrangement method.

The visual line input image Se3 is a support image for allowing the user to input a visual line. The visual line input image Se3 is a 2D image representing a blood vessel structure of an object obtained by plain imaging by this X-ray diagnostic apparatus. The description of a visual line rotating direction, a visual line angular interval, the number of visual lines, and the completion button Co is the same as that described with reference to FIG. 6A.

FIG. 7B is a view showing the third example of a visual line setting support screen after a plurality of visual lines are input.

Referring to FIG. 7B, when the user inputs a stereoscopic target position p3, a reference visual line B1 is automatically input. The support screen forming unit 35 then arranges a mark indicating the reference visual line B1. The reference visual line B1 is input, with a stereoscopic target position being p3, a visual line direction being a direction (a direction perpendicular to a slice of the visual line input image Se3) in which the user sees the currently displayed visual line input image Se3, and a display direction being the direction of the currently displayed visual line input image Se3. In addition, the user has input "vertical" as a visual line rotating direction, "15°" as a visual line angular interval, and "9" as the number of visual lines. The support screen forming unit 35 then arranges a line which passes through the mark indicating the reference visual line B1 and indicates a visual line rotating direction R2 in the longitudinal direction of the visual line input image Se3. The support screen forming unit 35 also arranges a plurality of marks respectively corresponding to a plurality of visual lines on the line indicating the visual line rotating direction R2 in accordance with the number of visual lines and the visual line angular interval which are input by the user. Referring to FIG. 7B, since "9" and "15°" are respectively input as the number of visual lines and a visual line angular interval, nine marks respectively corresponding to nine visual lines (B1 to B9 in FIG. 7B) including the reference visual line B1 are arranged. The nine marks are arranged at angular intervals of 15°. At this time, the support screen forming unit 35 decides the sizes of the nine marks in accordance with the angles formed with the reference visual line B1 with respect to the stereoscopic target position p3. This is because it is impossible to check depth directions on the visual line input image Se3 as a 2D image. For this reason, the support screen forming unit 35 arranges marks having sizes corresponding to the respective depth directions at nine positions respectively corresponding to the nine visual lines. For example, the mark corresponding to the visual line B5 is smaller than the mark corresponding to the visual line B2. With this arrangement, the visual line B5 indicates a direction in which the user sees the stereoscopic target position p3 from a deeper position on the visual line input image Se3 than the visual line B2. The visual line B5 is the fourth visual line from the reference visual line B1. For this reason, the angle formed by the visual line B5 and the direction of the reference visual line is 60°. The user can correct an input visual line by a mouse operation on the visual line input image Se3. For example, the user can correct the visual line B5 by moving the mark indicating the visual line B5 with the mouse. The visual line setting unit 22 sets a plurality of visual lines in response to the pressing of the completion button Co.

Although the method of inputting a plurality of visual lines has been described above, the visual line input image to be used is not limited to the above image as long as the coordinate system of a a visual line input image corresponds the coordinate system of the patient placed on the top 14. For example, the visual line input image to be used may be a human body model image imitating a human body. This is because a region of the patient placed on the top 14 can be roughly specified in the top coordinate system having a predetermined position on the top 14 as an origin if patient information such as the posture, body type, age, and sex of the patient is known. In addition, a visual line input image may be a 3D image or 2D image reconstructed based on the volume data acquired by another modality, e.g., an X-ray CT (Computed Tomography) apparatus. Positioning with this X-ray diagnostic apparatus can be performed by positioning with a feature point of an object.

The imaging position setting unit 23 executes imaging position setting processing based on the plurality of visual lines set by the visual line setting unit 22, together with the parallax conditions and the range of an ROI (Region of Interest) which are input by the user via the input unit 21. The imaging position setting processing is the processing of specifying the data of a left-eye imaging position and the data of a right-eye imaging position which correspond to a visual line. In addition, the imaging position setting unit 23 uses a trigonometry or the like to calculate a parallax based on an inter-pupil distance and a reference user distance. Imaging position setting processing will be described with reference to FIGS. 8A, 8B, 9A, and 9B.

FIGS. 8A and 8B are the first views for explaining imaging position setting processing by the imaging position setting unit 23 of the X-ray diagnostic apparatus according to this embodiment.

FIG. 8A is a view showing the first example of the positional relationship between a stereoscopic target position of the patient placed on the top 14, a visual line direction, and a display direction.

FIG. 8B is a view when FIG. 8A is viewed from the +Z-axis direction.

Assume that in FIGS. 8A and 8B, as in FIG. 4, an axis parallel to the long axis of the top 14 is defined as the Z-axis, an axis parallel to the short axis of the top 14 is defined as the X-axis, and an axis perpendicular to the top 14 surface is defined as the Y-axis. A stereoscopic target position is set to Po1, and the visual line direction of the stereoscopic target position Po1 is set to Ar1. In this case, for the sake of simplicity, assume that the stereoscopic target position Po1 included in a visual line 1 is located at the origin of the top coordinate system, and the visual line direction Ar1 included in the visual line 1 coincides with the Y-axis. Therefore, visual line angles corresponding to the visual line direction Ar1 are $\theta=0°$ and $\varphi=0°$. In addition, the left and up of the display direction included in the visual line 1 are respectively set to the +X-axis direction and the +Z-axis direction.

The imaging position setting unit 23 specifies, in accordance with a parallax, angles through which the visual line is tilted from the visual line direction Ar1 to the left-eye imaging position and the right-eye imaging position. Referring to FIGS. 8A and 8B, if, for example, the parallax is 3°, angles through which the visual line is tilted from the visual line direction Ar1 to the left-eye imaging position and the right-eye imaging position are both 1.5°. The imaging position setting unit 23 also specifies directions in which the visual line is tilted from the visual line direction Ar1 to the left-eye imaging position and the right-eye imaging position. Referring to FIGS. 8A and 8B, the left and up of the display direction are respectively set to the +X-axis direction and the +Z-axis target position. Therefore, the imaging position setting unit 23 sets a left-eye imaging position in a direction tilted 1.5° from the visual line direction Ar1 to the +X-axis direction. Likewise, the imaging position setting unit 23 sets a right-eye imaging position in a direction tilted 1.5° from the visual line direction Ar1 to the −X-axis direction. Referring to FIGS. 8A and 8B, the left-eye imaging position and the right-eye imaging position set by the above processing respectively correspond to Le1 and Ri1, respectively. The left-eye imaging position Le1 is defined by $\theta=0°$ and $\varphi=1.5°$. The right-eye imaging position Ri1 is defined by $\theta=180°$ and $\varphi=1.5°$. Note that the imaging position setting unit 23 specifies an imaging distance D1 based on the range of the ROI. With the above processing, the imaging position setting unit 23 can set the left-eye imaging position Le1 and the right-eye imaging position Ri1 corresponding to the visual line 1.

FIGS. 9A and 9B are the second views for explaining imaging position setting processing by the imaging position setting unit 23 of the X-ray diagnostic apparatus according to this embodiment.

FIG. 9A is a view showing the second example of the positional relationship between the stereoscopic target position of the patient placed on the top 14, a visual line direction, and a display direction.

FIG. 9B is a view when FIG. 9A is viewed from the +X-axis direction.

Assume that the same coordinate system, stereoscopic target position Po1, and visual line direction Ar1 as those in FIGS. 8A and 8B are set in FIGS. 9A and 9B. A difference from FIG. 8 resides in a display direction. The left and up of the display direction corresponding to the visual line 1 shown in FIG. 8 are respectively set to the +X-axis direction and the +Z-axis direction. In contrast to this, the left and up of the display direction corresponding to the visual line 2 shown in FIG. 9 are respectively set to the −Z-axis direction and the +X-axis direction.

The imaging position setting unit 23 specifies, in accordance with a parallax, angles through which the visual line is tilted from the visual line direction Ar1 to the left-eye imaging position and the right-eye imaging position. Referring to FIGS. 9A and 9B, if, for example, the parallax is 3°, angles through which the visual line is tilted from the visual line direction Ar1 to the left-eye imaging position and the right-eye imaging position are both 1.5°. The imaging position setting unit 23 also specifies, in accordance with a display direction, directions in which the visual line is tilted from the visual line direction Ar1 to the left-eye imaging position and the right-eye imaging position. Referring to FIGS. 9A and 9B, the left and up of the display direction are respectively set to the −Z-axis direction and the +X-axis direction. Therefore, the imaging position setting unit 23 sets a left-eye imaging position in a direction tilted 1.5° from the visual line direction Ar1 to the −Z-axis direction. Likewise, the imaging position setting unit 23 sets a right-eye imaging position in a direction tilted 1.5° from the visual line direction Ar1 to the +Z-axis direction. Referring to FIGS. 9A and 9B, the left-eye imaging position and the right-eye imaging position set by the above processing respectively correspond to Le2 and Ri2, respectively. The left-eye imaging position Le2 is defined by $\theta=270°$ and $\varphi=1.5°$. The right-eye imaging position Ri2 is defined by $\theta=90°$ and $\varphi=1.5°$. Note that the imaging position setting unit 23 specifies an imaging distance D2 based on the range of the ROI. With the above processing, the imaging position setting unit 23 can set the left-eye imaging position Le2 and the right-eye imaging position Ri2 corresponding to the visual line 2.

The imaging position setting unit 23 sets a plurality of left-eye imaging positions and a plurality of right-eye imaging positions corresponding to a plurality of visual lines (which will be collectively referred to as a plurality of imaging positions hereinafter) by repeatedly executing the above imaging position setting processing.

The sequence setting unit 24 sets a movement sequence for the C-arm 11 concerning the plurality of imaging positions set by the imaging position setting unit 23. As described above, an imaging position can be changed by independently rotating the C-arm 11 and the C-arm support mechanism 12 about a plurality of rotation axes. At this time, the sequence setting unit 24 specifies a plurality of rotational angle sets respectively corresponding to a plurality of imaging positions. A rotational angle set includes the data of the rotational angles of a plurality of rotation axes. The sequence setting unit 24 sets a movement sequence so as to reduce a rotation load on the mechanism when the C-arm 11 moves to each of a plurality of imaging positions. The rotation load on the mechanism is large in the following cases: 1) when reversal movement is performed; 2) when a rotation axis is changed; 3) when rotation is started; 4) when rotation is stopped; and 5) when the number of rotations of each rotation axis is large. Reversal movement indicates movement in which the C-arm 11 rotates in the forward direction, stops, and instantly starts rotating in the reverse direction. A change of a rotation axis occurs when the C-arm 11 rotates about the first rotation axis and then rotates about the first rotation axis and the second rotation axis during the rotation, or occurs when the C-arm 11 rotates about the first rotation, stops, and starts rotating about the second rotation axis. The sequence setting unit 24 sets a movement sequence based on rotation angle sets respectively corresponding to a plurality of imaging positions so as to reduce a rotation load on the mechanism.

The mechanism control unit 25 controls the moving unit 19 to move the C-arm 11 to the plurality of imaging positions set by the imaging position setting unit 23 in accordance with the movement sequence set by the sequence setting unit 24. Note that the mechanism control unit 25 may control the moving unit 19 to move the top 14 so as to move the top 14 relative to the C-arm 11. The mechanism control unit 25 specifies the coordinates of the current position of the C-arm 11 in the top coordinate system based on the rotational angle of each rotation axis associated with the movement of the C-arm 11, which is detected by the angle detection unit 20, and the movement amount of the top 14. The mechanism control unit 25 then specifies a rotational angle around each rotation axis to move the C-arm 11 from the current position to the next imaging position based on the coordinates of the current position of the C-arm 11 and the coordinates of the next imaging position. The mechanism control unit 25 controls the moving unit 19 based on the specified rotational angle around each rotation axis. A method of setting the movement sequence for the C-arm 11 by the sequence setting unit 24 and rotation axes for the movement of the C-arm 11 according to the set movement sequence will be described later.

The X-ray condition setting unit 26 sets X-ray conditions based on the X-ray conditions input by the user.

The X-ray control unit 27 controls each unit associated with X-ray imaging. More specifically, the X-ray control unit 27 controls the high voltage generation unit 16 in accordance with the X-ray conditions set by the X-ray condition setting unit 26 in synchronism with movement control on the C-arm 11 by the mechanism control unit 25. In this case, the X-ray control unit 27 executes an X-ray imaging operation by controlling both the high voltage generation unit 16 and the X-ray detection unit 18. The X-ray control unit 27 then controls the respective operations of the storage unit 31, the image generation unit 29, the preprocessing unit 28, and the like in synchronism with the X-ray imaging operation.

The preprocessing unit 28 executes preprocessing for the electrical signal output from the X-ray detection unit 18. Preprocessing includes, for example, various types of correction processing, amplification processing, and A/D conversion processing.

The image generation unit 29 generates X-ray image data based on the preprocessed electrical signal. More specifically, the image generation unit 29 generates a plurality of left-eye images respectively corresponding to a plurality of left-eye imaging positions and a plurality of right-eye images respectively corresponding to a plurality of right-eye imaging positions. The pixel value assigned to each pixel of an X-ray image is a value or the like corresponding to an X-ray attenuation coefficient concerning a material on an X-ray transmission path.

The control unit 30 is processing circuitry and includes a CPU (Central Processing Unit) and a memory circuit. The control unit 30 receives the instruction information input via the input unit 21, and temporarily stores it in the memory circuit. The control unit 30 controls each unit of the X-ray diagnostic apparatus based on the input information. More specifically, the control unit 30 associates left-eye images and right-eye images (to be referred to as parallax image sets hereinafter), of the plurality of left-eye image data and the plurality of right-eye image data generated by the image generation unit 29, which respectively correspond to visual lines. The control unit 30 then stores the data of a plurality of parallax image sets respectively corresponding to a plurality of visual lines in the storage unit 31.

The storage unit 31 is a semiconductor storage device such as a Flash SSD (Solid State Disk) as a semiconductor storage element, an HDD (Hard Desk Drive), or the like. The storage unit 31 stores the data of a plurality of images generated by the image generation unit 29. More specifically, the storage unit 31 stores the data of a plurality of parallax image sets respectively corresponding to a plurality of visual line directions, together with data concerning the visual line directions under the control of the control unit 30. In addition, the storage unit 31 stores data other than the data associated with the parallax image sets, for example, the data of X-ray conditions, the data of parallax conditions, the data of a human body diagram, and the data of a user information database. The user information database is a correspondence table associating a plurality of user IDs with a plurality of inter-pupil distances and a plurality of reference user positions.

The display control unit 32 reads out a parallax image set corresponding to a specific visual line direction from the storage unit 31 in accordance with a user instruction, and displays the image set on the display unit 33 so as to allow the user to stereoscopically recognize the image set at a specific position. In addition, the display control unit 32 reads out a plurality of parallax image sets corresponding to a plurality of visual line directions and displays the image sets on the display unit 33 (to be described later) so as to allow the user to stereoscopically recognize them as a moving image at a specific position in accordance with a user instruction. With these operations, the user can stereoscopically recognize a visual line direction concerning the object.

For example, in a naked-eye type two-parallax lenticular lens scheme, the display control unit 32 transmits a video signal obtained by vertically dividing each of a left-eye image and a right-eye image in a visual line direction concerning an object into strips to the display unit 33. The display unit 33 displays the left-eye image and the right-eye image divided into strips such that they are alternately arranged. The divided left-eye images and right-eye images are alternately arranged and displayed on the display unit 33. The display unit 33 has a lenticular lens on its display surface. A lenticular lens is a lens which changes the position that a visual line reaches depending on the position where the user sees. Adjusting the placement of the lenticular lens allows the right and left eyes to see only the right- and left-eye images, respectively, thereby allowing the user to stereoscopically recognize the visual line direction concerning the object.

In addition, in an eyeglass type frame sequential scheme, the display control unit 32 transmits a right-eye image signal corresponding to a left-eye image in the visual line direction concerning an object to the display unit 33 after a left-eye image signal corresponding to a left-eye image in the visual line direction concerning the object in one frame synchronization period. The display control unit 32 repeatedly executes the above video signal transmission processing in a specific cycle. The display unit 33 switches and displays images in a specific cycle based on the left-eye image signals and the right-eye image signals repeatedly transmitted from the display control unit 32. The user wears liquid crystal shutter eyeglasses and sees the display unit 33. The liquid crystal shutters alternately shut the left and right fields of view in synchronism with the image switching display operation of the display unit 33. The shutters of the eyeglasses open and close perfectly in synchronism with two images to allow the right eye to see only a right-eye image and allow the left eye to see only a left-eye image, thereby allowing the user to stereoscopically recognize the visual line direction concerning the object.

Although the display control unit 32 and the display unit 33 according to this embodiment have been described by taking the two stereoscopic vision schemes as examples, the embodiment can be applied to any stereoscopic vision schemes using parallax. In addition, the embodiment can be applied to any stereoscopic vision schemes which can use multi-parallax techniques.

A method of setting a movement sequence for the C-arm 11 by the sequence setting unit 24 and a method of controlling the moving unit 19 by the mechanism control unit 25 to move the C-arm 11 in accordance with a set movement sequence will be described with reference to FIGS. 10 to 13.

Figure 10A:
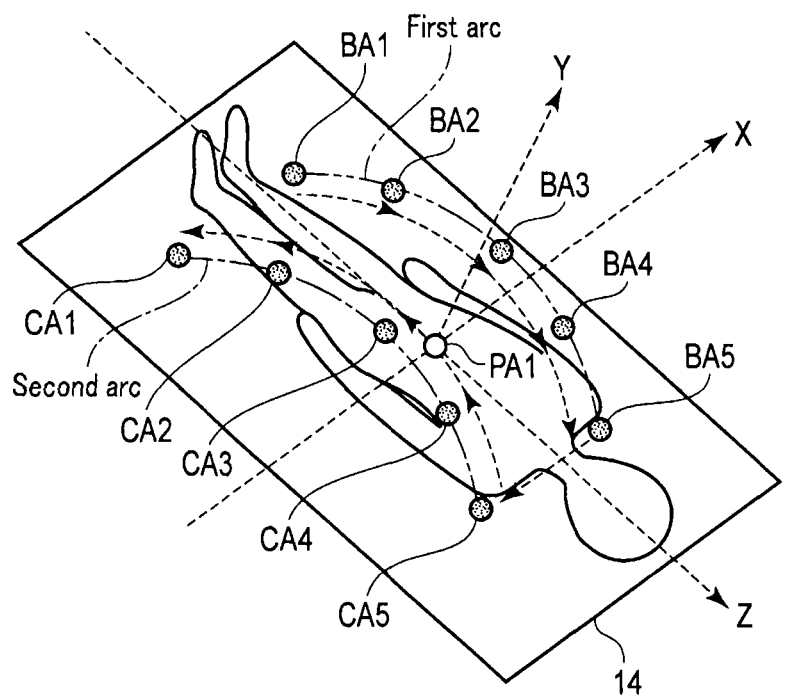
FIG. 10A is a perspective view showing the first example of a plurality of imaging positions.
Figure 10B:
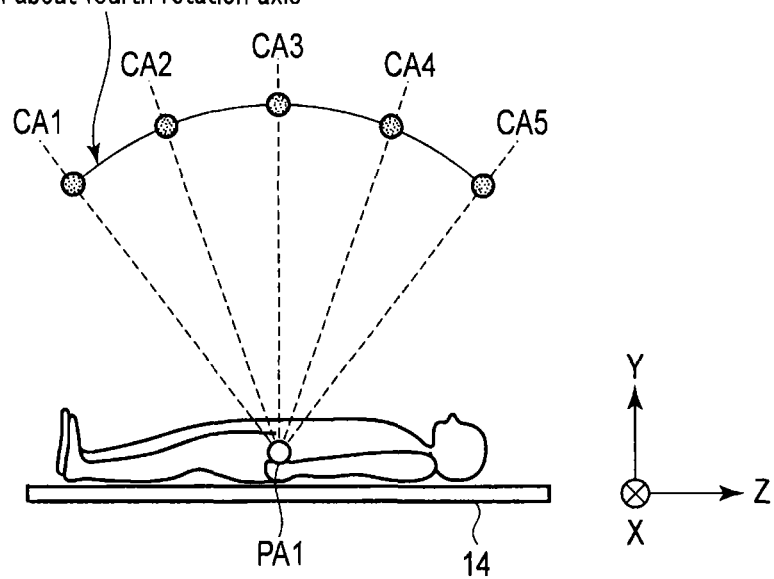
FIG. 10B is a view when
Figure 10C:
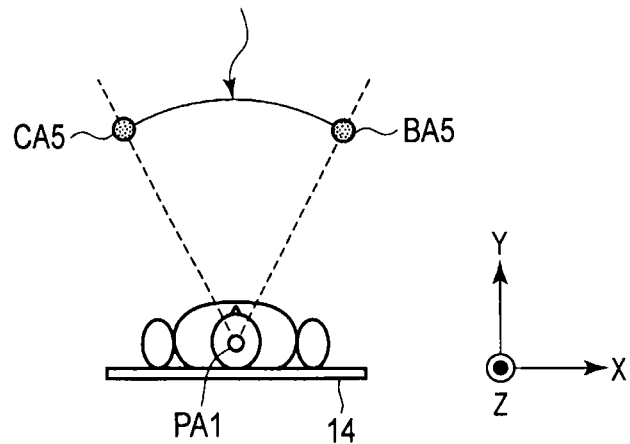
FIG. 10C is a view when

FIGS. 10A, 10B, and 10C are views showing the first example of a plurality of imaging positions set by the imaging position setting unit 23.

FIG. 10A is a perspective view of the first example of a plurality of imaging positions.

FIG. 10B is a view when FIG. 10A is viewed from the −X-axis.

FIG. 10C is a view when FIG. 10A is viewed from the +Z-axis.

Referring to FIG. 10, a plurality of visual lines are set with respect to a stereoscopic target position PA1. A plurality of left-eye imaging positions and a plurality of right-eye imaging positions respectively corresponding to a plurality of visual lines are set. The up and left of a display direction respectively correspond to the +Z-axis direction and the +X-axis direction. Therefore, the plurality of left-eye imaging positions correspond to imaging positions BA1 to BA5. The plurality of right-eye imaging positions correspond to imaging positions CA1 to CA5. The left-eye imaging position BA1 and the right-eye imaging position CA1 correspond to one visual line at the stereoscopic target position PA1. That is, FIG. 10 corresponds to a case in which a stereoscopic vision video centered on the stereoscopic target position PA1 is rotated in the longitudinal direction.

Referring to FIG. 10, a plurality of left-eye imaging positions (the imaging positions BA1 to BA5 in FIG. 10A) and a plurality of right-eye imaging positions (the imaging positions CA1 to CA5 in FIG. 10A) are respectively set at equal intervals on the first and second arcs. The first arc has the same shape as that of the second arc. In addition, the first and second arcs are centered on the stereoscopic target position PA1 and set along the Z-axis. A left-eye imaging position and a right-eye imaging position (e.g., the imaging positions BA5 and CA5 in FIG. 10A) which correspond to one visual line are set on an arc centered on the stereoscopic target position PA1.

The C-arm 11 can move along an arc centered on the stereoscopic target position PA1 by sliding rotation of the C-arm 11 about the fourth rotation axis. The C-arm 11 can move along an arc centered on the stereoscopic target position PA1 by the rotation of the arm holder 123 about the third rotation axis. Therefore, the C-arm 11 is moved from one left-eye imaging position to another left-eye imaging position by rotation about the fourth rotation axis. The C-arm 11 is moved from a left-eye imaging position corresponding to one visual line to a right-eye imaging position by rotation about the third rotation axis. The C-arm 11 is moved from one right-eye imaging position to another right-eye imaging position by rotation about the fourth rotation axis.

The sequence setting unit 24 sets a movement sequence so as to minimize the number of times of reversal movement. That is, if a movement sequence is in the order of the left-eye imaging position BA1, the right-eye imaging position CA1, the left-eye imaging position BA2, and the right-eye imaging position CA2, reversal movement about the third rotation axis occurs. Therefore, the sequence setting unit 24 sets a movement sequence so as to prevent repeated movement from a left-eye imaging position to a right-eye imaging position. More specifically, the sequence setting unit 24 sets a movement sequence in the order of the left-eye imaging position BA1, the right-eye imaging position CA1, the right-eye imaging position CA2, and the left-eye imaging position BA2. This sequence is set such that imaging is continuously performed at at least two imaging positions of the plurality of left-eye imaging positions or imaging is continuously performed at at least two imaging positions of the plurality of right-eye imaging positions. This eliminates the number of times of reversal movement.

In addition, a movement sequence may be set so as to minimize the number of times of reversal movement and minimize the number of times of changing a rotation axis. Referring to FIG. 10, the timing of changing a rotation axis is the time when the C-arm 11 is moved from a left-eye imaging position to a right-eye imaging position. The sequence setting unit 24 therefore sets a movement sequence such that after the C-arm 11 is moved to each of a plurality of left-eye imaging positions, the C-arm 11 is moved to each of a plurality of right-eye imaging positions.

More specifically, the mechanism control unit 25 controls the moving unit 19 to continuously move the C-arm 11 from the left-eye imaging position BA1 to the left-eye imaging position BA5. The moving unit 19 slides/rotates the C-arm 11 about the fourth rotation axis under the control of the mechanism control unit 25. While the C-arm 11 is translated from the left-eye imaging position BA1 to the left-eye imaging position BA5, a plurality of left-eye images respectively corresponding to a plurality of left-eye imaging positions are acquired. After a left-eye image corresponding to the left-eye imaging position BA5 is acquired, the rotation axis is changed. The mechanism control unit 25 controls the moving unit 19 to move the C-arm 11 from the left-eye imaging position BA5 to the right-eye imaging position CA5. The moving unit 19 rotates the arm holder 123 about the third rotation axis under the control of the mechanism control unit 25. When the C-arm 11 is moved to a position corresponding to the right-eye imaging position CA5, the rotation axis is changed. The mechanism control unit 25 controls the moving unit 19 to continuously move the C-arm 11 from the right-eye imaging position CA5 to the right-eye imaging position CA1. The moving unit 19 slides/rotates the C-arm 11 about the fourth rotation axis under the control of the mechanism control unit 25. While the C-arm 11 is translated from the right-eye imaging position CA5 to the right-eye imaging position CA1, a plurality of right-eye images respectively corresponding to a plurality of right-eye imaging positions are acquired. That is, the number of times of changing a rotation axis is one, which occurs when the C-arm 11 is moved from the left-eye imaging position BA5 to the right-eye imaging position CA5. In addition, the number of times of reversal movement is 0.

Figure 11A:
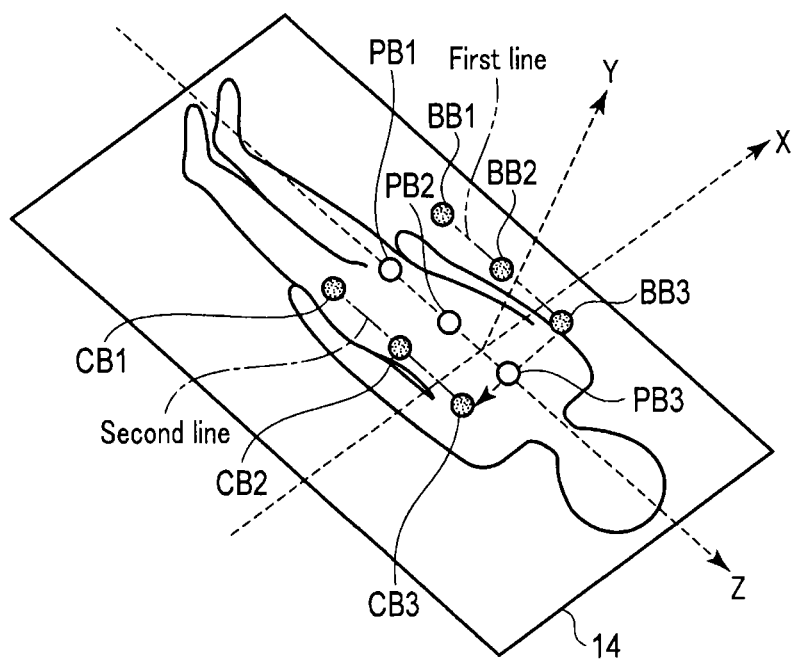
FIG. 11A is a perspective view showing the second example of a plurality of imaging positions.
Figure 11B:
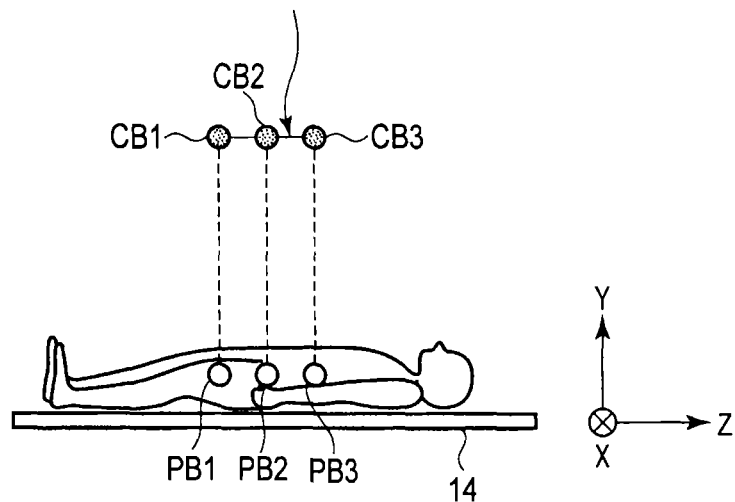
FIG. 11B is a view when
Figure 11C:
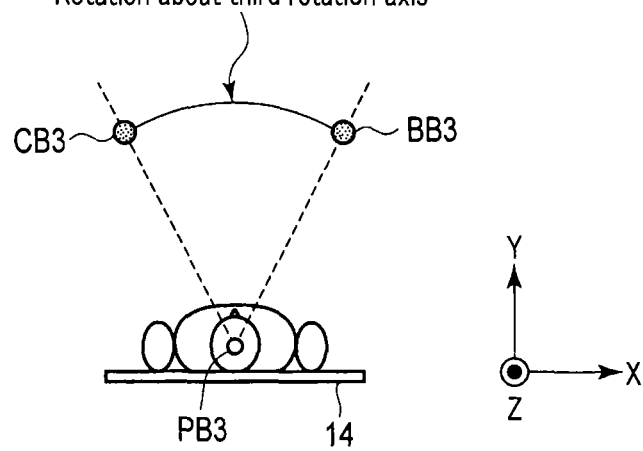
FIG. 11C is a view when

FIGS. 11A, 11B, and 11C are views showing the second example of a plurality of imaging positions set by the imaging position setting unit 23.

FIG. 11A is a perspective view of the second example of a plurality of imaging positions.

FIG. 11B is a view when FIG. 11A is viewed from the −X-axis.

FIG. 11C is a view when FIG. 11A is viewed from the +Z-axis.

Referring to FIG. 11, one visual line is set in correspondence with each of stereoscopic target positions PB1, PB2, and PB3. The plurality of visual lines are parallel to each other. A plurality of left-eye imaging positions and a plurality of right-eye imaging positions respectively corresponding to the plurality of visual lines are set. Assume that up and left of a display direction respectively correspond to the +Z-axis direction and the +X-axis direction. Therefore, the plurality of left-eye imaging positions correspond to imaging positions BB1 to BB3. The plurality of right-eye imaging positions correspond to imaging positions CB1 to CB3. The left-eye imaging position BB1 and the right-eye imaging position CB1 correspond to one visual line at the stereoscopic target position PB1. That is, FIG. 11 corresponds to a case in which a stereoscopic vision video is translated in the longitudinal direction.

Referring to FIG. 11, a plurality of left-eye imaging positions (the imaging positions BB1 to BB3 in FIG. 11) and a plurality of right-eye imaging positions (the imaging positions CB1 to CB3 in FIG. 11) are respectively set on the first and second lines on a plane parallel to the X-Z plane. In addition, a left-eye imaging position and a right-eye imaging position corresponding to one visual line are set on an arc centered on a stereoscopic target position. For example, the left-eye imaging position BB3 and the right-eye imaging position CB3 in FIG. 11 are set on an arc centered on the stereoscopic target position PB3.

The C-arm 11 can be translated with respect to a plane parallel to the X-Z plane by the rotation of the floor swivel arm 121 about the first rotation axis and the rotation of the stand 122 about the second rotation axis. Therefore, the C-arm 11 is moved from one left-eye imaging position to another left-eye imaging position by the rotation of the floor swivel arm 121 about the first rotation axis and the rotation of the stand 122 about the second rotation axis. The C-arm 11 is moved from a left-eye imaging position to a right-eye imaging position corresponding to one stereoscopic target position by rotation about the third or fourth rotation axis. The C-arm 11 is moved from one right-eye imaging position to another right-eye imaging position by the rotation of the floor swivel arm 121 about the first rotation axis and the rotation of the stand 122 about the second rotation axis.

The sequence setting unit 24 sets a movement sequence so as to minimize the number of times of reversal movement. That is, if the sequence setting unit 24 sets a movement sequence in the order of the left-eye imaging position BB1, the right-eye imaging position CB1, the left-eye imaging position BB2, and the right-eye imaging position CB2, reversal movement about the third rotation axis occurs. Therefore, the sequence setting unit 24 sets a movement sequence so as to prevent repeated movement from a left-eye imaging position to a right-eye imaging position. More specifically, the sequence setting unit 24 sets a movement sequence in the order of the left-eye imaging position BB1, the right-eye imaging position CB1, the right-eye imaging position CB2, and the left-eye imaging position BB2 such that imaging is continuously performed at at least two imaging positions of the plurality of left-eye imaging positions or imaging is continuously performed at at least two imaging positions of the plurality of right-eye imaging positions. This eliminates the number of times of reversal movement.

In addition, a movement sequence may be set so as to minimize the number of times of reversal movement and minimize the number of times of changing a rotation axis. Referring to FIG. 11, the timing of changing a rotation axis is the time when the C-arm 11 is moved from a left-eye imaging position to a right-eye imaging position. The sequence setting unit 24 therefore sets a movement sequence such that after the C-arm 11 is moved to each of a plurality of left-eye imaging positions, the C-arm 11 is moved to each of a plurality of right-eye imaging positions.

More specifically, the mechanism control unit 25 controls the moving unit 19 to continuously move the C-arm 11 from the left-eye imaging position BB1 to the left-eye imaging position BB3. The moving unit 19 moves the floor swivel arm 121 about the first rotation axis and rotates the stand 122 about the second rotation axis under the control of the mechanism control unit 25. While the C-arm 11 is translated from the left-eye imaging position BB1 to the left-eye imaging position BB3, a plurality of left-eye images respectively corresponding to a plurality of left-eye imaging positions are acquired. After a left-eye image corresponding to the left-eye imaging position BB3 is acquired, the rotation axis is changed. The mechanism control unit 25 controls the moving unit 19 to move the C-arm 11 from the left-eye imaging position BB3 to the right-eye imaging position CB3. The moving unit 19 rotates the arm holder 123 about the third rotation axis under the control of the mechanism control unit 25. When the C-arm 11 is moved to a position corresponding to the right-eye imaging position CB3, the rotation axis is changed. The mechanism control unit 25 controls the moving unit 19 to continuously move the C-arm 11 from the right-eye imaging position CB3 to the right-eye imaging position CB1. The moving unit 19 rotates the floor swivel arm 121 about the first rotation axis and rotates the stand 122 about the second rotation axis under the control of the mechanism control unit 25. While the C-arm 11 is translated from the right-eye imaging position CB3 to the right-eye imaging position CB1, a plurality of right-eye images respectively corresponding to a plurality of right-eye imaging positions are acquired. That is, the number of times of changing a rotation axis is one, which occurs when the C-arm 11 is moved from the left-eye imaging position BB3 to the right-eye imaging position CB3. In addition, the number of times of reversal movement is 0.

FIGS. 12A, 12B, and 12C are views showing the third example of a plurality of imaging positions set by the imaging position setting unit 23.

FIG. 12A is a perspective view of the third example of a plurality of imaging positions.

FIG. 12B is a view when FIG. 12A is viewed from the −X-axis.

FIG. 12C is a view when FIG. 12A is viewed from the +Z-axis.

Referring to FIG. 12, one visual line is set in correspondence with each of stereoscopic target positions PC1 to PC5. A plurality of visual lines differ in their visual line directions. A visual line direction corresponding to the stereoscopic target position PC2 and a visual line direction corresponding to the stereoscopic target position PC4 are tilted through the same angle in opposite directions with reference to a visual line direction corresponding to the stereoscopic target position PC3. Likewise, a visual line direction corresponding to the stereoscopic target position PC1 and a visual line direction corresponding to the stereoscopic target position PC5 are tilted through the same angle in opposite directions with reference to a visual line direction corresponding to the stereoscopic target position PC3. A plurality of left-eye imaging positions and a plurality of right-eye imaging positions respectively corresponding to a plurality of visual lines are set. Assume that up and left of each of the display directions included in a plurality of visual lines respectively correspond to the +Z-axis direction and the +X-axis direction. Therefore, the plurality of left-eye imaging positions correspond to imaging positions BC1 to BC5. The plurality of right-eye imaging positions correspond to imaging positions CC1 to CC5. The left-eye imaging position BC1 and the right-eye imaging position CC1 correspond to the visual line of the stereoscopic target position PC1. That is, FIG. 12 corresponds to a case in which a stereoscopic vision video is rotated in the longitudinal direction while the central position of the stereoscopic vision video is moved in the longitudinal direction.

Referring to FIG. 12, a plurality of left-eye imaging positions (the imaging positions BC1 to BC5 in FIG. 12) and a plurality of right-eye imaging positions (the imaging positions CC1 to CC5 in FIG. 12) are respectively set on the first and second orbits along the Z-axis. The first orbit has the same shape as that of the second orbit. Each imaging position has the same imaging distance. In addition, a left-eye imaging position and a right-eye imaging position which correspond to one visual line are set on an arc centered on the stereoscopic target position. For example, the imaging positions BC4 and CC4 in FIG. 12 are set on an arc centered on the stereoscopic target position PC4.

The C-arm 11 is moved from one left-eye imaging position to another left-eye imaging position by the rotation of the floor swivel arm 121 about the first rotation axis, the rotation of the stand 122 about the second rotation axis, and the sliding rotation of the C-arm 11 about the fourth rotation axis. The C-arm 11 is moved from a left-eye imaging position to a right-eye imaging position, which correspond to one stereoscopic target position, by rotation about the third rotation axis. The C-arm 11 is moved from one left-eye imaging position to another left-eye imaging position by the rotation of the floor swivel arm 121 about the first rotation axis, the rotation of the stand 122 about the second rotation axis, and the sliding rotation of the C-arm 11 about the fourth rotation axis.

The sequence setting unit 24 sets a movement sequence so as to minimize the number of times of reversal movement. That is, if the sequence setting unit 24 sets a movement sequence in the order of the left-eye imaging position BC1, the right-eye imaging position CC1, the left-eye imaging position BC2, and the right-eye imaging position CC2, reversal movement about the third or fourth rotation axis occurs. Therefore, the sequence setting unit 24 sets a movement sequence so as to prevent repeated movement from a left-eye imaging position to a right-eye imaging position. More specifically, the sequence setting unit 24 sets a movement sequence such that imaging is performed continuously at at least two left-eye imaging positions or right-eye imaging positions, like the right-eye imaging position BC1, the right-eye imaging position CC1, the right-eye imaging position CC2, and the left-eye imaging position BC2. This eliminates the number of times of reversal movement.

In addition, a movement sequence may be set so as to minimize the number of times of reversal movement and minimize the number of times of changing a rotation axis. Referring to FIG. 12, the timing of changing a rotation axis is the time when the C-arm 11 is moved from a left-eye imaging position to a right-eye imaging position. The sequence setting unit 24 therefore sets a movement sequence such that after the C-arm 11 is moved to each of a plurality of left-eye imaging positions, the C-arm 11 is moved to each of a plurality of right-eye imaging positions.

More specifically, the mechanism control unit 25 controls the moving unit 19 to continuously move the C-arm 11 from the left-eye imaging position BC1 to the left-eye imaging position BC5. The moving unit 19 moves the floor swivel arm 121 about the first rotation axis, rotates the stand 122 about the second rotation axis, and slides/rotates the C-arm 11 about the fourth rotation axis under the control of the mechanism control unit 25. While the C-arm 11 is translated from the left-eye imaging position BC1 to the left-eye imaging position BC5, a plurality of left-eye images respectively corresponding to a plurality of left-eye imaging positions are acquired. After a left-eye image corresponding to the left-eye imaging position BC5 is acquired, the rotation axis is changed. The mechanism control unit 25 controls the moving unit 19 to move the C-arm 11 from the left-eye imaging position BC5 to the right-eye imaging position CC5. The moving unit 19 rotates the arm holder 123 about the third rotation axis under the control of the mechanism control unit 25. When the C-arm 11 is moved to a position corresponding to the right-eye imaging position CC5, the rotation axis is changed. The mechanism control unit 25 controls the moving unit 19 to continuously move the C-arm 11 from the right-eye imaging position CC5 to the right-eye imaging position CC1. The moving unit 19 rotates the floor swivel arm 121 about the first rotation axis, rotates the stand 122 about the second rotation axis, and slides/rotates the C-arm 11 about the fourth rotation axis under the control of the mechanism control unit 25. While the C-arm 11 is translated from the right-eye imaging position CC5 to the right-eye imaging position CC1, a plurality of right-eye images respectively corresponding to a plurality of right-eye imaging positions are acquired. That is, the number of times of changing a rotation axis is one, which occurs when the C-arm 11 is moved from the left-eye imaging position BC5 to the right-eye imaging position CC5. In addition, the number of times of reversal movement is 0.

FIG. 13 is a view showing the fourth example of a plurality of imaging positions set by the imaging position setting unit 23.

Referring to FIG. 13, visual lines D1, D2, and D3 are set with respect to a stereoscopic target position PD1. A plurality of left-eye imaging positions and a plurality of right-eye imaging positions respectively corresponding to the plurality of visual lines are set. Assume that up and left of a display direction respectively correspond to the +Z-axis direction and the +X-axis direction. Therefore, the plurality of left-eye imaging positions correspond to imaging positions BD1 to BD3. The plurality of right-eye imaging positions correspond to imaging positions CD1 to CD3. The left-eye imaging position BD1 and the right-eye imaging position CD1 correspond to the visual line D1 at the stereoscopic target position PD1. That is, FIG. 13 corresponds to a case in which a stereoscopic vision video centered on the stereoscopic target position PD1 is rotated in the lateral direction.

Referring to FIG. 13, a plurality of left-eye imaging positions (the imaging positions BD1 to BD3 in FIG. 13) and a plurality of right-eye imaging positions (the imaging positions CD1 to CD3 in FIG. 13) are respectively set on the same arc. This arc is parallel to the X-axis.

The C-arm 11 can be moved along the arc centered on the stereoscopic target position PD1 by sliding rotation of the C-arm 11 about the fourth rotation axis. In addition, the C-arm 11 can be moved along an arc centered on the stereoscopic target position PD1 by the rotation of the arm holder 123 about the third rotation axis. Therefore, the C-arm 11 can be moved to each of a plurality of left-eye imaging positions and a plurality of right-eye imaging positions by rotation about the third rotation axis or the fourth rotation axis.

The sequence setting unit 24 sets a movement sequence so as to minimize the number of times of reversal movement. That is, if a movement sequence is in the order of the left-eye imaging position BD1, the right-eye imaging position CD1, the left-eye imaging position BD2, and the right-eye imaging position CD2, reversal movement about the third or fourth rotation axis occurs. Therefore, the sequence setting unit 24 sets a movement sequence so as to prevent repeated movement from a left-eye imaging position to a right-eye imaging position. More specifically, if the sequence setting unit 24 sets a plurality of imaging positions on the same arc, like the right-eye imaging position CD1, the left-eye imaging position BD1, the right-eye imaging position CD2, and the left-eye imaging position BD2, the sequence setting unit 24 sets a movement sequence so that rotation is from one imaging position on the arc in one direction. This eliminates the number of times of reversal movement.

Note that the method of setting a movement sequence shown in FIGS. 10 to 13 is an example, and so is the method of controlling the moving unit 19 for movement in accordance with a set movement sequence. The sequence setting unit 24 can set a movement sequence based on the number of times of reversal movement, the number of times of changing a rotation axis, the number of times of starting rotation, the number of times of stopping rotation, and the total number of rotations of each rotation axis as long as it is possible to reduce a rotation load on the mechanism. In addition, the moving unit 19 need not rotate the C-arm 11, the floor swivel arm 121, the stand 122, and the arm holder 123 to translate the C-arm 11. For example, the moving unit 19 may move the top 14 to translate the C-arm 11.

A series of processing operations using the X-ray diagnostic apparatus according to this embodiment will be described next with reference to FIG. 14.

Figure 14:
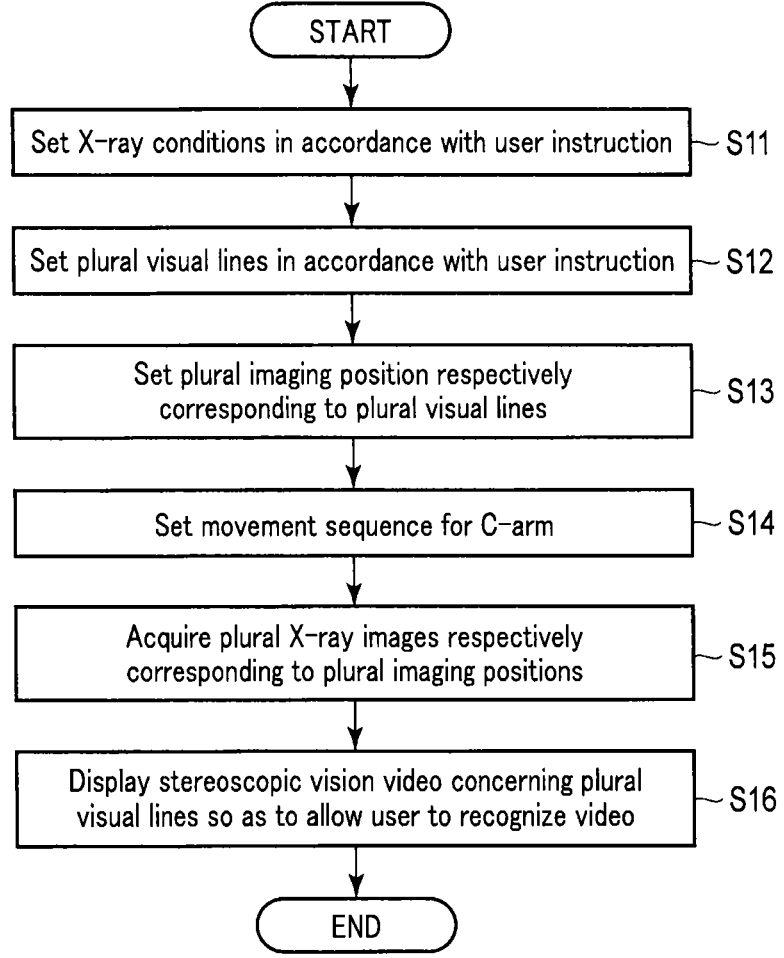
FIG. 14 is a flowchart showing an example of a series of processing operations using the X-ray diagnostic apparatus according to this embodiment.

FIG. 14 is a flowchart showing an example of a series of processing operations using the X-ray diagnostic apparatus according to this embodiment.
(Step S11)
The X-ray condition setting unit 26 sets X-ray conditions based on the X-ray conditions input by the user via the input unit 21.

(Step S12)
The visual line setting unit 22 sets a plurality of visual lines in accordance with a user operation on the visual line setting support screen via the input unit 21.
(Step S13)
The imaging position setting unit 23 sets a plurality of imaging positions (a plurality of left-eye imaging positions and a plurality of right-eye imaging positions) based on the parallax conditions (an inter-pupil distance and a reference user distance) input by the user via the input unit 21 and the plurality of visual lines set by the visual line setting unit 22.
(Step S14)
The sequence setting unit 24 sets a movement sequence for the C-arm 11 so as to reduce a rotation load on the mechanism based on the plurality of imaging positions. The sequence setting unit 24 sets a movement sequence based on, for example, the number of times of reversal movement and the number of times of changing a rotation axis.
(Step S15)
The moving unit 19 moves the C-arm 11 to each of the plurality of imaging positions in accordance with the movement sequence set by the sequence setting unit 24 under the control of the mechanism control unit 25. Each unit acquires a plurality of left-eye images respectively corresponding to a plurality of left-eye imaging positions and a plurality of right-eye images respectively corresponding to a plurality of right-eye imaging positions. The control unit 30 stores a plurality of parallax image sets (a data set of the data of a plurality of left-eye images and the data of a plurality of right-eye images respectively corresponding to a plurality of visual lines) in the storage unit 31.
(Step S16)
The display control unit 32 reads out a parallax image set corresponding to a specific visual line from the storage unit 31 in accordance with a user instruction. This image set is displayed on the display unit 33 to allow the user to recognize a stereoscopic vision video corresponding to the specific visual line at the reference user position.

The following effects can be obtained by the X-ray diagnostic apparatus according to this embodiment described above.

The X-ray diagnostic apparatus according to this embodiment can set a plurality of visual lines in accordance with a user instruction on a visual line setting support screen. Based on the plurality of set visual lines, a plurality of left-eye imaging positions and a plurality of right-eye imaging positions respectively corresponding to the plurality of visual lines can be set. It is then possible to acquire a plurality of left-eye images and a plurality of right-eye images respectively corresponding to the plurality of set left-eye imaging positions and the plurality of set right-eye imaging positions. The display control unit 32 displays a parallax image set corresponding to the set visual lines on the display unit 33. When visually recognizing the display unit 33 at the reference user position, the user can recognize a stereoscopic vision video corresponding to the set visual lines. A visual line can be changed as needed in accordance with a user instruction.

This X-ray diagnostic apparatus can decide a movement sequence of a plurality of imaging positions in this series of processing operations so as to reduce a load on the mechanism. The X-ray diagnostic apparatus decides a movement sequence based on, for example, at least one of the number of times of reversal movement and the number of times of changing a rotation axis. For example, the X-ray diagnostic apparatus sets a movement sequence so as to move the C-arm 11 to each of a plurality of right-eye imaging positions after moving the C-arm 11 to each of a plurality of left-eye imaging positions. According to this example of a movement sequence, it is possible to minimize the number of times of switching a rotation axis concerning the movement of the C-arm 11.

The X-ray diagnostic apparatus according to this embodiment can therefore image an object continuously or intermittently from a plurality of directions while suppressing a load on the mechanism associated with the rotation of the C-arm. This effect is especially effective in diagnosis, medical treatment, or the like using a stereoscopic vision video.

The above described "processing circuitry" means, for example, a central processing unit (CPU), a graphics processing unit (GPU), an application specific integrated circuit (ASIC), a programmable logical device (e.g., a simple programmable logic device (SPLD), a complex programmable logic device (CPLD), and a field programmable gate array (FPGA)), or the like.

Each function (each component) in the present embodiment is not necessary to be corresponded to a single processing circuit and may be realized by a plurality of processing circuits. To the contrary, for example, at least two functions (at least two components) may be realized by a single processing circuit. Further, a plurality of functions (a plurality of components) may be realized by a single processing circuit.

Some embodiments have been described above. However, these embodiments are presented merely as examples and are not intended to restrict the scope of the embodiments. This embodiment has exemplified stereoscopic vision. However, the present embodiments can be applied to an examination or the like in which imaging, other than imaging for stereoscopic vision, is performed at a plurality of imaging positions. In this case as well, the X-ray diagnostic apparatus can decide a movement sequence of a plurality of imaging positions so as to reduce a load on the mechanism based on the number of times of reversal movement and the number of times of changing a rotation axis. These embodiments can be carried out in various other forms, and various omissions, replacements, and alterations can be made without departing from the spirit of the invention. These embodiments and their modifications are also incorporated in the scope and the spirit of the invention as well as in the invention described in the claims and their equivalents.

The invention claimed is:

1. An X-ray diagnostic apparatus comprising:
   an X-ray tube configured to generate X-rays;
   an X-ray detector configured to detect X-rays generated from the X-ray tube and transmitted through an object;
   a supporting arm configured to support the X-ray tube and the X-ray detector in directions to face each other;
   a moving mechanism configured to move the supporting arm around a plurality of rotation axes;
   processing circuitry configured to set an imaging sequence concerning a plurality of left-eye imaging positions with respect to the object and a plurality of right-eye imaging positions respectively corresponding to the plurality of left-eye imaging positions and configured to control the moving mechanism to move the supporting arm in accordance with the set imaging sequence,
   wherein the imaging sequence includes a sequence of continuously performing imaging at at least two of the plurality of left-eye imaging positions or a sequence of continuously performing imaging at at least two of the plurality of right-eye imaging positions.

2. The X-ray diagnostic apparatus of claim 1, wherein the imaging sequence is a sequence in which after imaging is performed at one set of the plurality of left-eye imaging positions and the plurality of right-eye imaging positions, imaging is performed at the other set.

3. The X-ray diagnostic apparatus of claim 1, wherein an orbit along which the supporting arm moves to the plurality of left-eye imaging positions has substantially the same shape as that of an orbit along which the supporting arm moves to the plurality of right-eye imaging positions.

4. The X-ray diagnostic apparatus of claim 1, wherein an orbit along which the supporting arm moves to the plurality of left-eye imaging positions and an orbit along which the supporting arm moves to the plurality of right-eye imaging positions have arcuated shapes.

5. The X-ray diagnostic apparatus of claim 1, wherein the processing circuitry sets the plurality of left-eye imaging positions and the plurality of right-eye imaging positions based on a plurality of visual lines concerning the object, which are input by the user.

6. The X-ray diagnostic apparatus of claim 5, further comprising an input interface circuitry configured to input the plurality of visual lines in accordance with an operation by the user on a visual line setting support screen.

7. The X-ray diagnostic apparatus of claim 6, wherein the visual line setting support screen comprises a 3D image or a 2D image concerning the object.

8. An X-ray diagnostic apparatus comprising:
   an X-ray tube configured to generate X-rays;
   an X-ray detector configured to detect X-rays generated from the X-ray tube and transmitted through an object;
   a supporting arm configured to hold the X-ray tube and the X-ray detector in directions to face each other;
   a moving mechanism configured to move the supporting arm around a plurality of rotation axes;
   processing circuitry configured to decide an imaging sequence of imaging a plurality of imaging positions with respect to the object based on the number of times of reversal movement of the supporting arm and configured to control the moving mechanism to move the supporting arm in accordance with the decided imaging sequence.

9. The X-ray diagnostic apparatus of claim 8, wherein the imaging sequence comprises an imaging sequence which minimizes the number of times of reversal movement of the supporting arm.

10. The X-ray diagnostic apparatus of claim 8, wherein the reversal movement comprises movement in which the supporting arm which has moved in a forward direction stops and instantly starts moving in a reverse direction.

* * * * *